(12) United States Patent
Zhou et al.

(10) Patent No.: US 10,466,383 B2
(45) Date of Patent: Nov. 5, 2019

(54) METHOD FOR USING NEUTRON INTERACTION CROSS SECTION TO INTERPRET NEUTRON MEASUREMENTS

(71) Applicant: Schlumberger Technology Corporation, Sugar Land, TX (US)

(72) Inventors: Tong Zhou, Sugar Land, TX (US); Christian Stoller, Princeton Junction, NJ (US); James Leslie Thornton, Princeton Junction, NJ (US); David Alan Rose, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 237 days.

(21) Appl. No.: 14/726,050

(22) Filed: May 29, 2015

(65) Prior Publication Data
US 2016/0349398 A1    Dec. 1, 2016

(51) Int. Cl.
*G01V 5/10*        (2006.01)
*G01N 33/24*       (2006.01)

(52) U.S. Cl.
CPC ............... *G01V 5/10* (2013.01); *G01V 5/107* (2013.01); *G01V 5/108* (2013.01); *G01N 33/24* (2013.01); *G01V 5/104* (2013.01)

(58) Field of Classification Search
CPC ......... G01V 5/10; G01V 5/101; G01V 5/105; G01V 5/107

(Continued)

(56) References Cited

U.S. PATENT DOCUMENTS 4,464,569 A * 8/1984 Flaum .................... G01V 5/102
                                              250/269.6
4,645,926 A   2/1987 Randall
(Continued)

FOREIGN PATENT DOCUMENTS

EP          2426516 A2      3/2012
WO     WO2010135618 A2     11/2010
(Continued)

OTHER PUBLICATIONS

Hertzog, Neutron-Excited Gamma-Ray Spectrometry for Well Logging, IEEE Transactions on Nuclear Science, vol. NS-26, No. 1, Feb. (Year: 1979).*
(Continued)

*Primary Examiner* — Michael J Dalbo
(74) *Attorney, Agent, or Firm* — Trevor G. Grove

(57) ABSTRACT

A method for determining a fractional volume of at least one component of a formation includes entering into a computer a number of detected radiation events resulting from imparting neutrons into the formation at an energy level of at least 1 million electron volts (MeV). The detected radiation events correspond to at least one of an energy level of the imparted neutrons and thermal or epithermal energy neutrons. A measurement of at least one additional petrophysical parameter of the formation is made. The at least one additional petrophysical parameter measurement and at least one of a fast neutron cross-section and a thermal neutron cross-section determined from the detected radiation events are used in the computer to determine the fractional volume of the at least one component of the formation. In another embodiment, the fast neutron cross-section and the thermal neutron cross-section may be used on combination to determine the fractional volume.

20 Claims, 15 Drawing Sheets

(58) Field of Classification Search
USPC .......................................................... 702/8
See application file for complete search history.

(56) References Cited

U.S. PATENT DOCUMENTS

| | | | |
|---|---|---|---|
| 5,293,410 A | 3/1994 | Chen et al. | |
| 5,498,960 A * | 3/1996 | Vinegar | G01V 3/32 324/303 |
| 5,539,225 A | 7/1996 | Loomis et al. | |
| 5,608,215 A * | 3/1997 | Evans | G01V 5/101 250/254 |
| 5,699,246 A | 12/1997 | Plasek et al. | |
| 5,804,820 A * | 9/1998 | Evans | G01V 5/101 250/269.2 |
| 5,909,772 A | 6/1999 | Merkel et al. | |
| 6,703,606 B2 * | 3/2004 | Adolph | G01V 5/104 250/269.1 |
| 6,754,586 B1 | 6/2004 | Adolph et al. | |
| 6,884,994 B2 | 4/2005 | Simonetti et al. | |
| 7,667,192 B2 * | 2/2010 | Fricke | G01V 5/107 250/266 |
| 8,471,197 B2 * | 6/2013 | Inanc | E21B 47/10 250/269.6 |
| 9,268,056 B2 | 2/2016 | Zhou et al. | |
| 9,310,515 B2 | 4/2016 | Zhou et al. | |
| 9,995,842 B2 | 6/2018 | Zhou | |
| 2002/0170348 A1 | 11/2002 | Roscoe et al. | |
| 2004/0128073 A1 | 7/2004 | Radtke et al. | |
| 2006/0226351 A1 | 10/2006 | Stoller et al. | |
| 2006/0284066 A1 | 12/2006 | Jacobson | |
| 2007/0023626 A1 | 2/2007 | Riley et al. | |
| 2009/0210161 A1 | 8/2009 | Duenckel et al. | |
| 2011/0001040 A1 | 1/2011 | Smith, Jr. et al. | |
| 2011/0213555 A1 | 9/2011 | Kopal et al. | |
| 2011/0284731 A1 | 11/2011 | Roscoe et al. | |
| 2011/0313669 A1 | 12/2011 | Thornton | |
| 2012/0016588 A1 | 1/2012 | Evans et al. | |
| 2012/0126106 A1 | 5/2012 | Zhou et al. | |
| 2012/0148004 A1 | 6/2012 | Caruso et al. | |
| 2012/0197529 A1 | 8/2012 | Stephenson et al. | |
| 2012/0215451 A1 * | 8/2012 | Husser | E21B 47/101 702/11 |
| 2013/0105678 A1 | 5/2013 | Wilson et al. | |
| 2013/0166223 A1 * | 6/2013 | Triplett | G21D 3/001 702/23 |
| 2013/0282288 A1 * | 10/2013 | Quinn | G01V 3/38 702/7 |
| 2014/0042311 A1 * | 2/2014 | Zhou | G01V 5/102 250/269.8 |
| 2014/0088877 A1 | 3/2014 | Ellis et al. | |
| 2014/0129149 A1 * | 5/2014 | Gzara | G01V 11/00 702/11 |
| 2014/0343856 A1 | 11/2014 | Zhou et al. | |
| 2015/0226874 A1 * | 8/2015 | Inanc | G01V 5/107 250/263 |
| 2015/0247948 A1 | 9/2015 | Zhou et al. | |
| 2015/0268376 A1 | 9/2015 | Zhou et al. | |
| 2015/0331141 A1 | 11/2015 | Grau et al. | |
| 2016/0003025 A1 | 1/2016 | Beekman et al. | |
| 2016/0003969 A1 | 1/2016 | Zhou et al. | |
| 2016/0349398 A1 | 12/2016 | Zhou et al. | |
| 2016/0349399 A1 | 12/2016 | Zhou | |
| 2017/0160425 A1 | 6/2017 | Miles et al. | |
| 2017/0227671 A1 | 8/2017 | Zhou | |

FOREIGN PATENT DOCUMENTS

| | | |
|---|---|---|
| WO | WO2012012101 A2 | 1/2012 |
| WO | WO2012012120 A2 | 1/2012 |
| WO | WO2012083210 A2 | 6/2012 |

OTHER PUBLICATIONS

International Seach Report and Written Opinion Issued in the related PCT Application PCT/US2013/034343, dated Jul. 11, 2013 (8 pages).

International Preliminary Report on patentability Issued in the related PCT Application PCT/US2013/034343, dated Oct. 1, 2014 (6 pages).

European Search Report issued in the related EP Application 13769611.8, dated Mar. 3, 2016 (5 pages).

Communication pursuant to Article 94(3) issued in the related EP Application 13769611.8, dated Mar. 23, 2016 (6 pages).

Robert Freedman, et al., A modern method for using databases to obtain accurate solutions to complex reservoir characterization problems, SPE Reservoir Evaluation & Engineering, Dec. 31, 2011, SPE 147169, pp. 1-15.

International Seach Report and Written Opinion Issued in the related PCT Application PCT/US2014/037672, dated Sep. 2, 2014 (14 pages).

International Preliminary Report on patentability Issued in the related PCT Application PCT/US2014/037672, dated Nov. 17, 2015 (10 pages).

Office Action issued in Related U.S. Appl. No. 13/895,189 dated Dec. 17, 2018, 23 pages.

* cited by examiner

METHOD FOR USING NEUTRON INTERACTION CROSS SECTION TO INTERPRET NEUTRON MEASUREMENTS

CROSS-REFERENCE TO RELATED APPLICATIONS

Not Applicable.

STATEMENT REGARDING FEDERALLY SPONSORED RESEARCH OR DEVELOPMENT

Not applicable.

NAMES TO THE PARTIES TO A JOINT RESEARCH AGREEMENT

Not Applicable.

BACKGROUND

This disclosure is related to the field of neutron well logging measurements for determining petrophysical properties of subsurface formations traversed by a wellbore. More specifically, the disclosure relates to using various neutron cross section values determined from neutron measurements to determine one or more petrophysical parameters of such formations.

Various neutron based measurements have been used to evaluate characteristics of subsurface formations from a wellbore since at least the 1950s. Neutrons can interact with subsurface formations in different ways. They can be scattered elastically, which means kinetic energy and momentum are conserved; they can be scattered inelastically, which means certain nuclei go into an excited state while kinetic energy is lost; they can also be captured by a nucleus to form a new nucleus; it is also possible that the neutron interaction causes a nuclear reaction resulting in the emission of one or more nucleons from the target nucleus. The probability of a neutron interacting with a nucleus is measured by the respective interaction cross section, which is a function of many parameters, such as incident neutron energy, outgoing neutron energy (if a neutron emerges from the interaction), scattering angle, interaction type and interactive nucleus type, among others. Thus, neutrons can enable measurement of many different formation properties due to the variety and complexity of their interactions.

An important wellbore neutron measurement known in the art is the thermal neutron die-away measurement. This is a measure of how fast thermal neutrons disappear. If the rate of disappearance ("decay") is approximated by an exponential function then the decay exponent ("decay constant") can be used to directly determine the formation thermal neutron capture cross section. In the oil and gas industry the macroscopic neutron capture cross section of the formation is called "sigma". Typically this cross section is measured in capture units (c.u.), where 1 capture unit is equal to 1000 $cm^{-1}$.

Another important wellbore neutron measurement known in the art is the neutron porosity measurement. The basic principle of such measurement is to impart high energy neutrons (typically several MeV depending on the source type) into the formation and measure the thermal (or epithermal) neutron flux at a certain distance from the source. The detector can be either a neutron detector or a gamma ray detector (measuring neutron induced gamma rays as an indirect measurement of the neutron flux). This measurement is very sensitive to the hydrogen content in the formation because hydrogen is the most effective neutron moderator among all elements. High hydrogen content can slow down neutrons to thermal energy (0.025 eV at room temperature) before they can travel very far. Thus, HI (Hydrogen Index) and porosity (fresh water filled) may be used to interpret the measurement. A limitation of the neutron porosity measurement is that it is accurate only for water filled, clean (clay free) single lithology (such as sandstone, limestone and dolomite) formations. Some other environmental conditions need special treatment, such as gas-filled porosity, shale, and complex lithology. In addition, the thermal neutron porosity measurement is sensitive to various environment effects including temperature and borehole and formation salinity.

Slowing-Down Length (Ls) is a parameter that describes how far a fast neutron travels on average before it is slowed down to thermal energy. It has been used in the past to interpret the neutron porosity measurement as well. The tool response can be predicted accurately, but the limitation is that Ls does not follow a volumetric mixing law. Thus, this technique is not widely used by petrophysicists.

SUMMARY

One aspect of the disclosure relates to a method for determining a fractional volume of at least one component of a formation. Methods according to this aspect of the disclosure include entering into a computer a number of detected radiation events resulting from imparting neutrons into the formation at an energy level of at least 1 million electron volts (MeV). The detected radiation events correspond to at least one of an energy level of the imparted neutrons, and thermal or epithermal energy neutrons. A method according to the present aspect of the disclosure includes at least one of, (i) using a fast neutron cross-section and a thermal neutron cross-section determined from the detected radiation events to determine a fractional volume of the at least one component of the formation, and (ii) using a measurement of at least one additional petrophysical parameter and using (a) the measurement of the at least one petrophysical parameters and (b) at least one of the fast neutron cross-section and the thermal neutron cross-section t determine the fractional volume of the at least one component of the formation.

Other aspects and advantages will be apparent from the description and claims that follow.

DETAILED DESCRIPTION

Figure 1A:
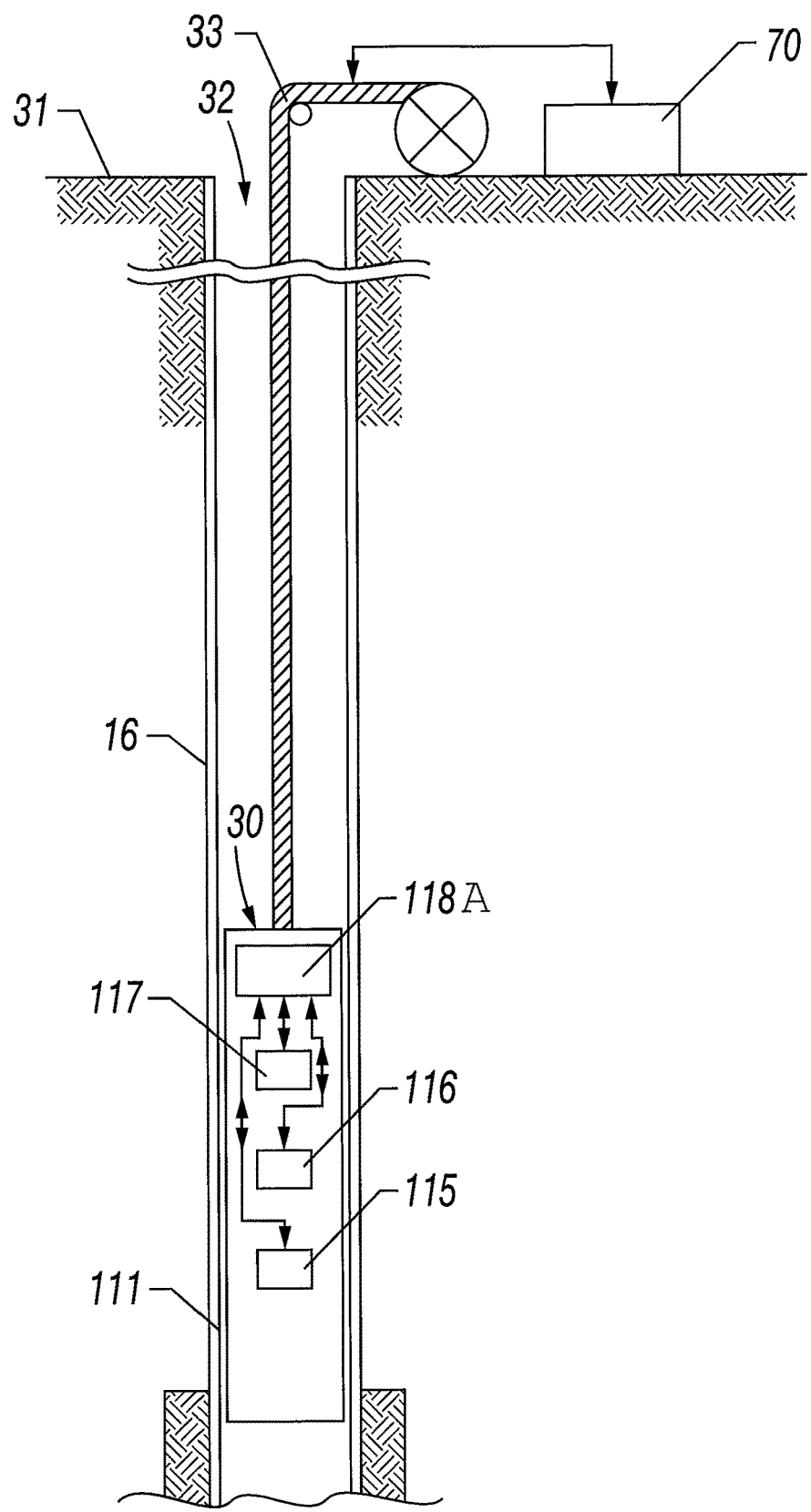
FIG. 1A shows an example well logging instrument conveyed through a wellbore by an electrical cable ("wireline").

FIG. 1A shows an example well logging instrument 30. The measurement components of the instrument 30 may be disposed in a housing 111 shaped and sealed to be moved along the interior of a wellbore 32. The instrument housing 111 may contain at least one energy source 115, e.g., a neutron source such as electrically operated pulsed neutron source ("source"), and one or more detectors 116, 117 each disposed at different axial spacings from the source 115. The source 115 may emit neutron radiation. Shielding (not shown) may be applied between the source 115 and the detectors 116, 117 to reduce direct transmission of neutrons from the source 115 to the detectors 116, 117. Thus, detected radiation may be characterized at each of a plurality of distances from the source 115, and thus have different lateral response (depth of investigation) into the formations surrounding the wellbore 32. In some examples, two or more different types of well logging instrument, each having a different type of source and different types of corresponding detectors may be included in the same instrument assembly of "tool string."

The instrument housing 111 maybe coupled to an armored electrical cable 33 that may be extended into and retracted from the wellbore 32. The wellbore 32 may or may not include metal pipe or casing 16 therein. The cable 33 conducts electrical power to operate the instrument 30 from a surface 31 deployed recording system 70, and signals from the detectors 116, 117 may be processed by suitable circuitry 118A for transmission along the cable 33 to the recording system 70. The recording system 70 may include a processor, computer or computer system as will be explained below with reference to FIG. 1C for analysis of the detected signals as well as devices for recording the signals communicated along the cable 33 from the instrument 30 with respect to depth and/or time.

The well logging tool described above can also be used, for example, in logging-while-drilling ("LWD") equipment. As shown, for example, in FIG. 1B, a platform and derrick 210 are positioned over a wellbore 212 that may be formed in the Earth by rotary drilling. A drill string 214 may be suspended within the borehole and may include a drill bit 216 attached thereto and rotated by a rotary table 218 (energized by means not shown) which engages a kelly 220 at the upper end of the drill string 214. The drill string 214 is typically suspended from a hook 222 attached to a traveling block (not shown). The kelly 220 may be connected to the hook 222 through a rotary swivel 224 which permits rotation of the drill string 214 relative to the hook 222. Alternatively, the drill string 214 and drill bit 216 may be rotated from the surface by a "top drive" type of drilling rig.

Drilling fluid or mud 226 is contained in a mud pit 228 adjacent to the derrick 210. A pump 230 pumps the drilling fluid 226 into the drill string 214 via a port in the swivel 224 to flow downward (as indicated by the flow arrow 232) through the center of the drill string 214. The drilling fluid exits the drill string via ports in the drill bit 216 and then circulates upward in the annular space between the outside of the drill string 214 and the wall of the wellbore 212, as indicated by the flow arrows 234. The drilling fluid 226 thereby lubricates the bit and carries formation cuttings to the surface of the earth. At the surface, the drilling fluid is returned to the mud pit 228 for recirculation. If desired, a directional drilling assembly (not shown) could also be employed.

A bottom hole assembly ("BHA") 236 may be mounted within the drill string 214, preferably near the drill bit 216. The BHA 236 may include subassemblies for making measurements, processing and storing information and for communicating with the Earth's surface. Such measurements may correspond to those made using the instrument string explained above with reference to FIG. 1A. The bottom hole assembly is typically located within several drill collar lengths of the drill bit 216. In the illustrated BHA 236, a stabilizer collar section 238 is shown disposed immediately above the drill bit 216, followed in the upward direction by a drill collar section 240, another stabilizer collar section 242 and another drill collar section 244. This arrangement of drill collar sections and stabilizer collar sections is illustrative only, and other arrangements of components in any implementation of the BHA 236 may be used. The need for or desirability of the stabilizer collars will depend on drilling conditions as well as on the demands of the measurement.

Figure 1B:
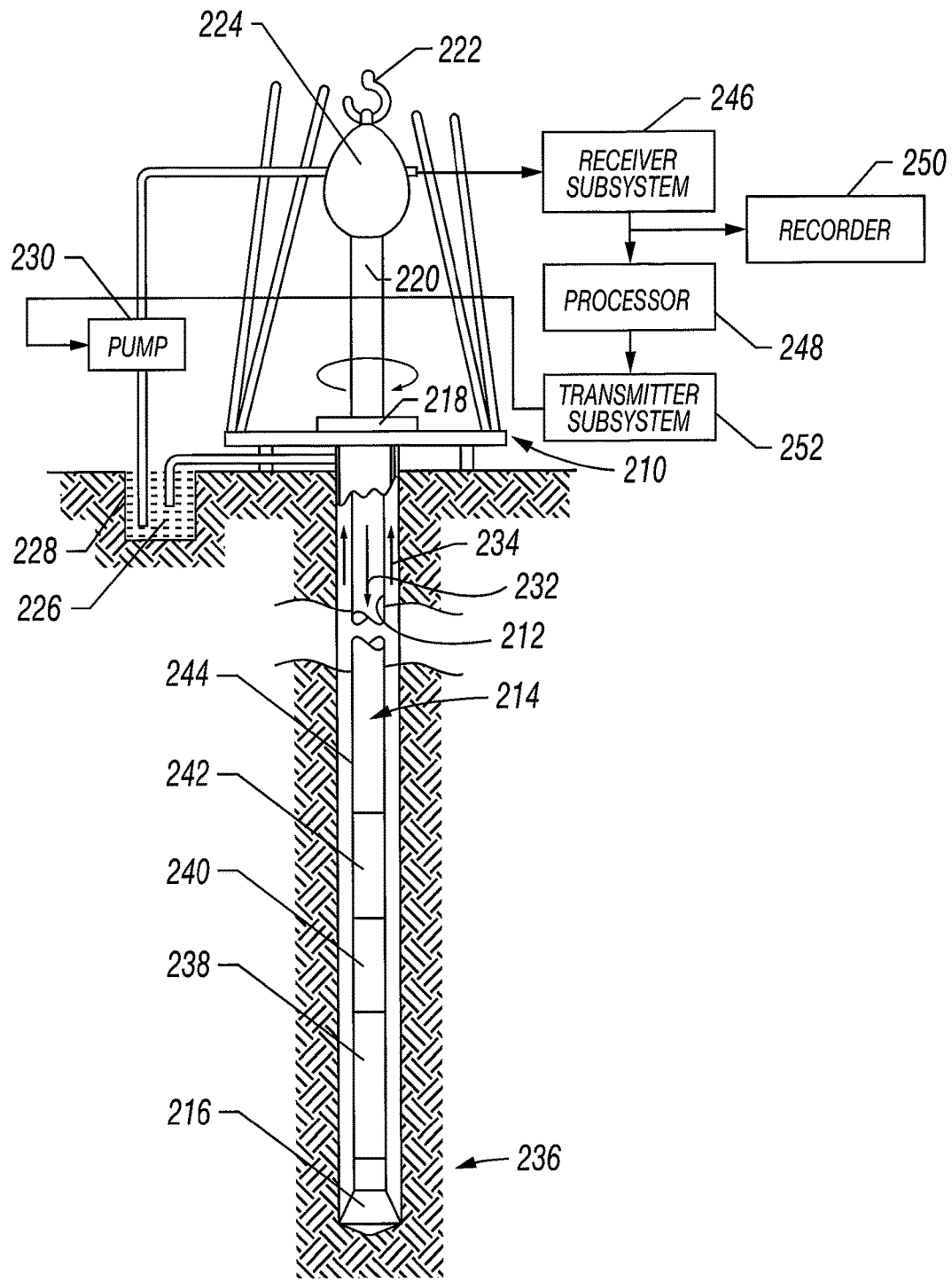
FIG. 1B shows an example logging while drilling instrument on a drill string.

In the arrangement shown in FIG. 1B, the components of the well logging instrument may be located in the drill collar section 240 above the stabilizer collar 238. Such components could, if desired, be located closer to or farther from the drill bit 216, such as, for example, in either stabilizer collar section 238 or 242 or the drill collar section 244.

The BHA 236 may also include a telemetry subassembly (not shown) for data and control communication with the Earth's surface. Such telemetry subassembly may be of any suitable type, e.g., a mud pulse (pressure or acoustic) telemetry system, wired drill pipe, etc., which receives output signals from LWD measuring instruments in the BHA 236 (including the one or more radiation detectors) and transmits encoded signals representative of such outputs to the surface where the signals are detected, decoded in a receiver subsystem 246, and applied to a processor 248 and/or a recorder 250. The processor 248 may comprise, for example, a suitably programmed general or special purpose processor. A surface transmitter subsystem 252 may also be provided for establishing downward communication with the bottom hole assembly.

The BHA 236 can also include conventional acquisition and processing electronics (not shown) comprising a microprocessor system (with associated memory, clock and timing circuitry, and interface circuitry) capable of timing the operation of the accelerator and the data measuring sensors, storing data from the measuring sensors, processing the data and storing the results, and coupling any desired portion of the data to the telemetry components for transmission to the surface. The data may also be stored in the instrument and retrieved at the surface upon removal of the drill string. Power for the LWD instrumentation may be provided by battery or, as known in the art, by a turbine generator disposed in the BHA 236 and powered by the flow of drilling fluid. The LWD instrumentation may also include directional sensors (not shown separately) that make measurements of the geomagnetic orientation or geodetic orientation of the BHA 236 and the gravitational orientation of the BHA 236, both rotationally and axially.

The foregoing computations may be performed on a computer system such as one shown in the processor at 248 in FIG. 1B, or in the surface unit 70 in FIG. 1A. However, any computer or computers may be used to equal effect.

Figure 1C:
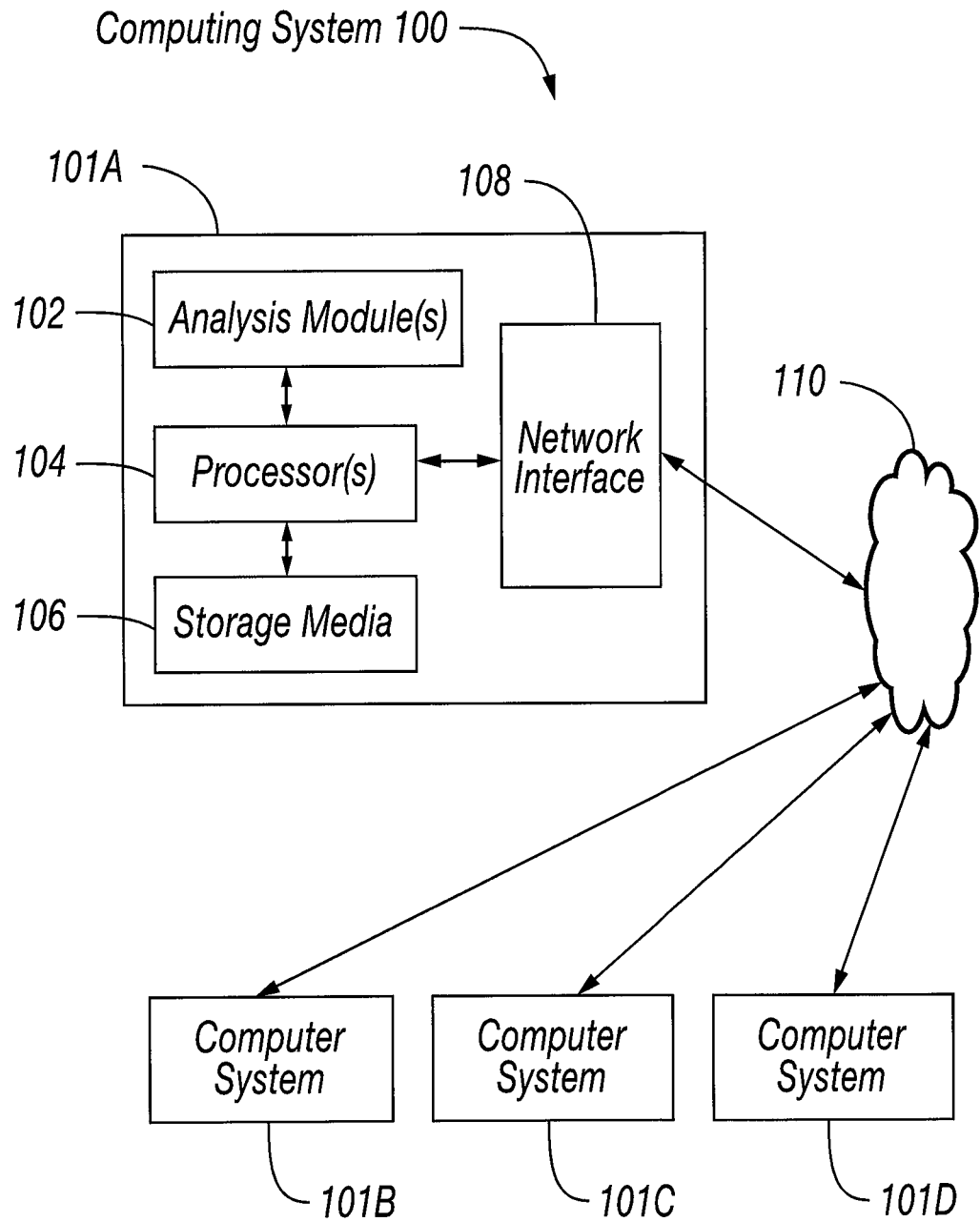
FIG. 1C shows an example computer system that may be used in some implementations.

FIG. 1C shows an example computing system 100 in accordance with some embodiments for carrying out example methods such as those to be explained below with reference to FIGS. 2 through 11. The computing system 100 can be an individual computer system 101A or an arrangement of distributed computer systems. The computer system 101A includes one or more analysis modules 102 that are configured to perform various tasks according to some embodiments, such as the tasks described above. To perform these various tasks, an analysis module 102 executes independently, or in coordination with, one or more processors 104, which is (or are) connected to one or more storage media 106. The processor(s) 104 is (or are) also connected to a network interface 108 to allow the computer system 101A to communicate over a data network 110 with one or more additional computer systems and/or computing systems, such as 101B, 101C, and/or 101D (note that computer systems 101B, 101C and/or 101D may or may not share the same architecture as computer system 101A, and may be located in different physical locations, e.g. computer systems 101A and 101B may be on a ship underway on the ocean, in a well logging unit disposed proximate a wellbore drilling, while in communication with one or more computer systems such as 101C and/or 101D that are located in one or more data centers on shore, other ships, and/or located in varying countries on different continents). Any one or more of the computer systems may be disposed in the well logging instrument (whether wireline as in FIG. 1A or LWD as in FIG. 1B).

A processor can include a microprocessor, microcontroller, processor module or subsystem, programmable integrated circuit, programmable gate array, digital signal processor (DSP), or another control or computing device.

The storage media 106 can be implemented as one or more non-transitory computer-readable or machine-readable storage media. Note that while in the embodiment of FIG. 1C storage media 106 is depicted as within computer system 101A, in some embodiments, storage media 106 may be distributed within and/or across multiple internal and/or external enclosures of computing system 101A and/or additional computing systems. Storage media 106 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system 100 is only one example of a computing system, and that computing system 100 may have more or fewer components than shown, may combine additional components not depicted in the embodiment of FIG. 1C, and/or computing system 100 may have a different configuration or arrangement of the components depicted in FIG. 1C. The various components shown in FIG. 1C may be implemented in hardware, software, or a combination of both hardware and software, including one or more signal processing and/or application specific integrated circuits.

Further, the steps in the methods described above may be implemented by running one or more functional modules in information processing apparatus such as general purpose processors or application specific chips, such as ASICs, FPGAs, PLDs, SOCs, or other appropriate devices. These modules, combinations of these modules, and/or their combination with general hardware are all included within the scope of protection of the invention.

Figure 1D:
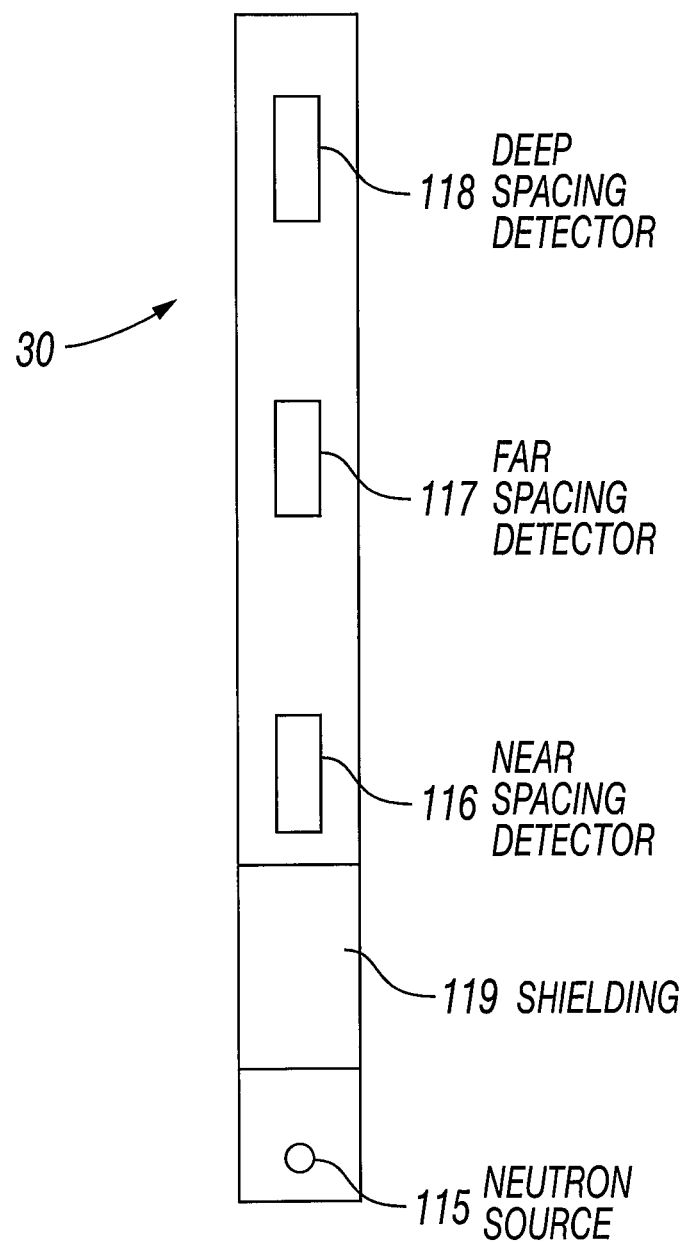
FIG. 1D shows a schematic representation of an example dual detector neutron well logging instrument.

FIG. 1D shows a schematic cross section of an example neutron well logging instrument structure. Three detectors 116, 117, 118 at various longitudinal spacings from a neutron source 115 are indicated, but for some embodiments a single detector may suffice. The detectors 116, 117, 118 may be fast neutron detectors, thermal neutron detectors, epithermal neutron detectors, gamma ray detectors, or combinations thereof. The foregoing may also include detectors which are sensitive to both neutrons and gamma rays, in which the neutron and gamma ray detection events can be distinguished. Shielding 119 between the source and the detectors reduces or prevents the direct passage of radiation from the neutron source to the detectors 116, 117 and 118. The neutron source 115 may be a radioisotope source, such as $^{241}$AmBe or $^{252}$Cf, or a pulsed neutron generator. The pulsed neutron generator may be based on the deuterium-tritium reaction (with source energy of 14.1 MeV, the deuterium-deuterium reaction (with a source energy of about 2.45 MeV) or any other suitable reaction. Methods according to the present disclosure can be applied to any form of neutron logging tools with the above described detector and/or neutron source options.

FIGS. 2A through 2D show the basic neutron microscopic cross sections of a few common earth elements, i.e., hydrogen, carbon, oxygen and silicon, respectively. In terms of neutron well logging applications, the most relevant neutron interaction types with formation materials are elastic scattering, inelastic scattering, and neutron capture, which are shown in FIGS. 2A through 2D. The x-axis indicates the incident neutron energy, ranging from thermal (0.025 eV) to 20 MeV on a logarithmic scale. The foregoing range covers substantially all neutron energy levels used in neutron well logging methods known in the art. The y-axis represents the neutron microscopic cross section on a logarithmic scale, with units of barns per atom. As can be observed in FIGS. 2A through 2D, all the three neutron cross sections, i.e., inelastic scattering shown respectively at curves 123A, 125A and 127A (in FIGS. 2B, 2C and 2D, respectively), elastic scattering shown at curves 121, 123, 125 and 127 and capture at curves 122, 124, 126 and 128 all vary as a function of incident neutron energy.

Figure 2A:
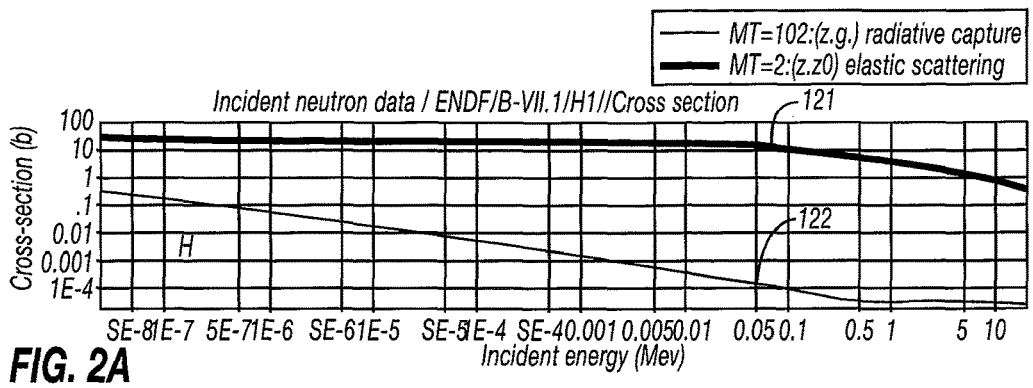
FIGS. 2A through 2D show fundamental neutron microscopic cross sections as a function of energy for common earth elements.
Figure 2B:
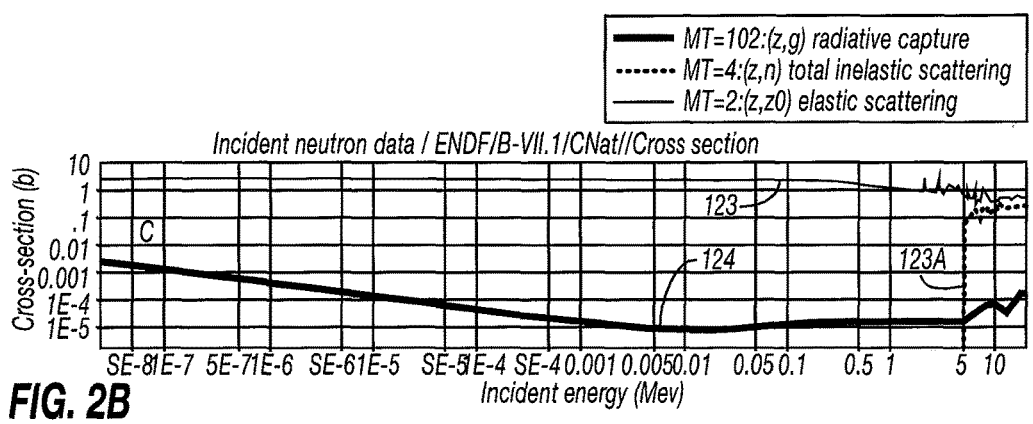
Figure 2C:
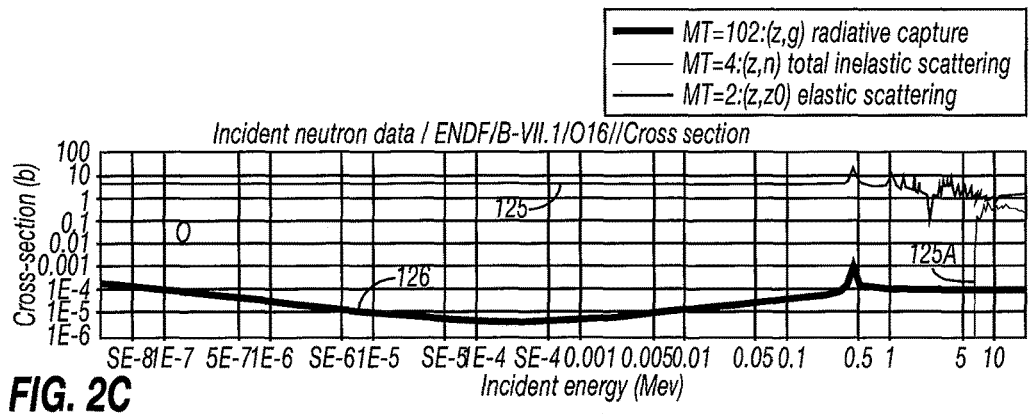
Figure 2D:
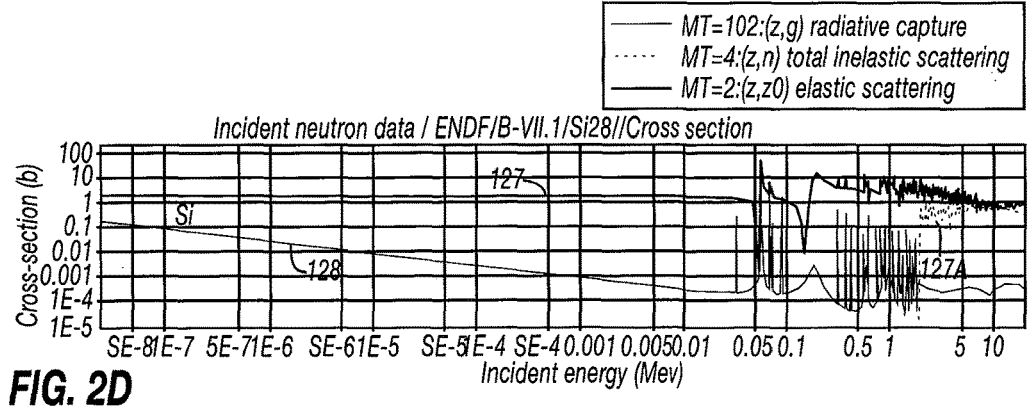

The capture cross section is typically low for neutrons at the million electron volt (MeV) energy level and above. The multiple peaks (for example, 0.05 to 1 MeV region in FIG. 2D) observable in FIGS. 2B, 2C and 2D are resonance peaks. The resonance energies are determined by the available excited states of nuclei with a certain number of protons and neutrons. Generally speaking, a heavier nucleus (with many protons and neutrons) will have lower resonance energies, and vice versa. The extreme example is the hydrogen nucleus, which has only a ground state with one proton and no neutron, so there is no resonance peak. Below the resonance energy region, the capture cross section typically increases proportionally to 1/v, where v is the neutron velocity. For a thermal neutron die-away measurement (equivalent to a thermal neutron capture cross section or "sigma" measurement), source neutrons with original energy in a range of a few MeV to more than about ten MeV will be slowed down very quickly to thermal energy and reach an equilibrium state. The capture cross section at thermal energy is typically a few orders of magnitude higher than at higher energy. The chance of a neutron being captured before it reaches thermal equilibrium is therefore very low. Because of this fact, the capture cross section at thermal energy is used in neutron sigma measurement well logging known in the art to interpret the thermal neutron die-away measurement. Following the same principle, methods according to the present disclosure expand the foregoing concept to other types of neutron interaction cross sections.

For a neutron porosity measurement, the source neutrons are slowed down partially through elastic scattering and partially through inelastic scattering from the initial source energy (above 1 MeV) all the way to thermal energy. The elastic/inelastic scattering cross sections in all the energy levels from the source energy to thermal energy are part of this process. Thus, it may be difficult to pick just one quantity or value to interpret the measurement. By further analyzing the cross section data, one can observe that elastic scattering has a larger effect on neutron energy reduction than inelastic scattering. This is because of the relative number of inelastic and elastic scattering events. Although a neutron can lose a lot of energy (~MeV) by a single inelastic scattering interaction, this can only occur at high neutron energy levels (typically >1 MeV). Below the 1-MeV energy threshold, inelastic scattering substantially does not occur. Thus, in its lifetime from emission by the source to reduction to thermal energy a neutron may only have a single inelastic scattering event. On the other hand, elastic scattering can occur at any energy and its probability is therefore a lot higher than for inelastic scattering. As a first order approximation, one can pick the elastic cross section as the variable to interpret a neutron porosity measurement. One step further, if one observes the elastic cross section carefully, one may notice that below a certain energy level, the elastic cross section is no longer a function of neutron energy. For example, below 0.05 MeV and above 1 eV, the hydrogen elastic cross section (FIG. 2A) is constant. It starts increasing again below 1 eV as energy decreases. This is because elastic scattering in this energy region is just like billiard ball scattering in classical physics; the probability is independent of the incident velocity. Below 1 eV, the neutron energy is close to the energy of the thermal movement of atoms. Fortuitously for purposes of methods according to the present disclosure, most of the scattering events for neutron slowing down occur in the energy region from 1 eV to 0.05 MeV. Thus, methods according to the present disclosure may use this energy independent elastic scattering cross section to interpret neutron porosity measurements. There are some approximations in such methods. Methods according to the present disclosure may neglect inelastic scattering, resonance scattering, and the variation of the elastic scattering cross section above about 0.05 MeV. Thus, one may or may not need to use other quantities, such as bulk density, to improve the accuracy of the interpreted measurements.

In order to take the neutron energy loss per scattering event into account, one can also use the "moderating power", which is sometimes called "slowing down power", to interpret the neutron porosity measurement. The concept of moderating power is commonly used in nuclear reactor physics. One can find more details in, Duderstadt, James J, "Nuclear Reactor Analysis", ISBN 0-471-22363-8.

$$\text{ModeratingPower} = \xi \cdot \Sigma_s \quad (1)$$

The definition of Moderating Power (MP) is shown in Eq. 1, where $\xi$ is the mean lethargy gain per neutron collision, and $\Sigma_s$ is the macroscopic elastic scattering cross section. Lethargy, which is a measure of the relative energy loss, is defined in Eq. 2 below.

$$\xi = 1 - \frac{(A-1)^2}{2A} \cdot \ln\left(\frac{A+1}{A-1}\right) \quad (2)$$

where A is the atomic mass.
Thus, $$MP = \xi \cdot \Sigma_s \quad (3)$$
$$= \left[1 - \frac{(A-1)^2}{2A} \cdot \ln\left(\frac{A+1}{A-1}\right)\right] \cdot \Sigma_s$$

MP is in effect a weighted scattering cross section, with the weight being a function of the atomic mass of the scattering nucleus. MP follows a volumetric mixing law.

Eq. 4 shows one way to compute the macroscopic cross section from microscopic cross section for any element. $\Sigma$ is the macroscopic cross section; $\sigma$ is the microscopic cross section; $\rho$ is the bulk density; A is the atomic mass; and $N_a$ is Avogadro's constant (approximately $6.02 \times 10^{23}$ mol$^{-1}$). For a material containing more than one element, Eq. 5 may be used to combine the macroscopic cross sections of multiple elements. $\Sigma_{total}$ is the material's macroscopic cross section; $\Sigma_i$ is the i$^{th}$ element's macroscopic cross section; $f_i$ is the volume fraction of the i$^{th}$ element; N is the total number of elements. Thus, the macroscopic cross section follows a volumetric mixing law as shown in Eq. 5.

$$\Sigma = \sigma \cdot AtomDensity \quad (4)$$
$$= \sigma \cdot \frac{\rho}{A} \cdot N_a$$
$$\Sigma_{total} = \sum_{i=1:N} (f_i \cdot \Sigma_i) \quad (5)$$

Figure 3:
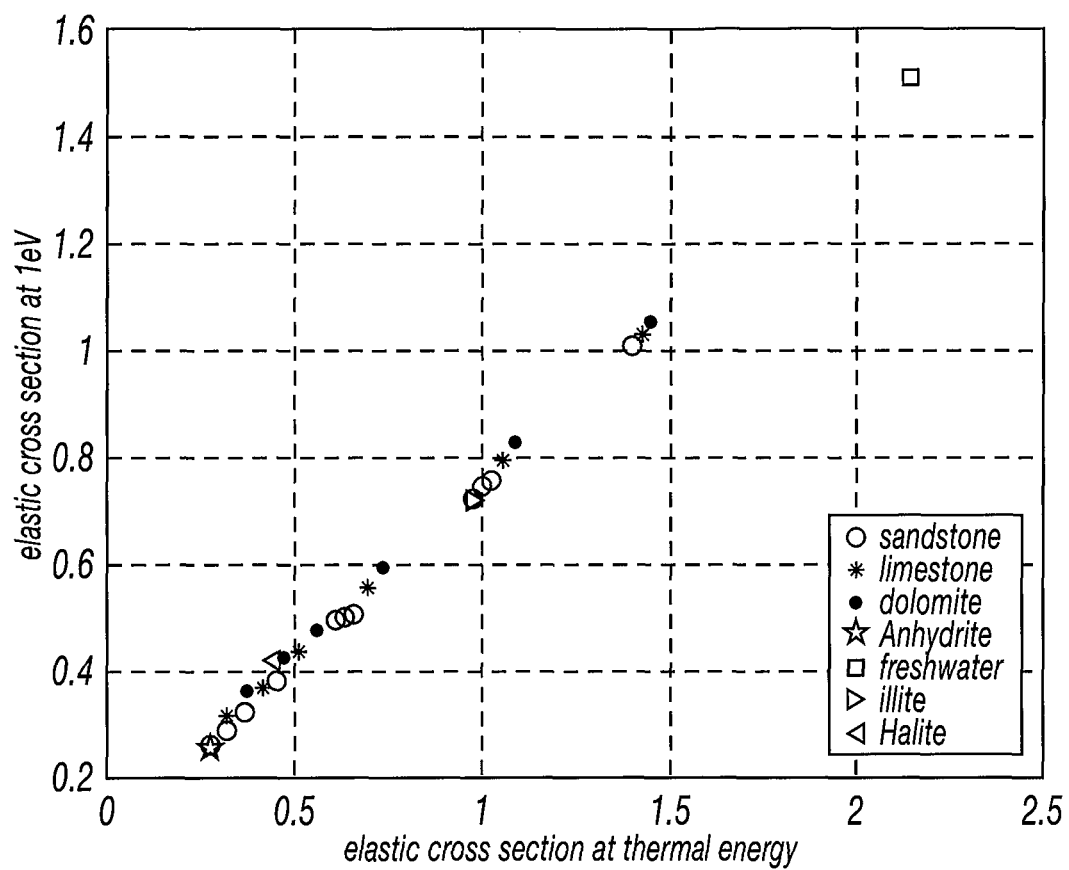
FIG. 3 shows a cross plot of neutron elastic scattering cross section ($cm^{-1}$) at thermal neutron energy and a 1-eV neutron energy for different lithologies and porosities.

FIG. 3 shows a graph of the correlation between the macroscopic neutron elastic scattering cross sections at two different neutron energies, 1 eV and thermal energy (0.025 eV at 25° C.). Although the elastic cross section values are different at each energy level, they are almost 100% correlated and will be so for many different formation conditions. Thus, one can choose to use either of the elastic scattering cross sections at 1 eV or at thermal energy to predict a neutron tool response. In the present embodiment of the disclosure, the neutron elastic scattering cross section at thermal energy may be used to demonstrate the example method.

Figure 4:
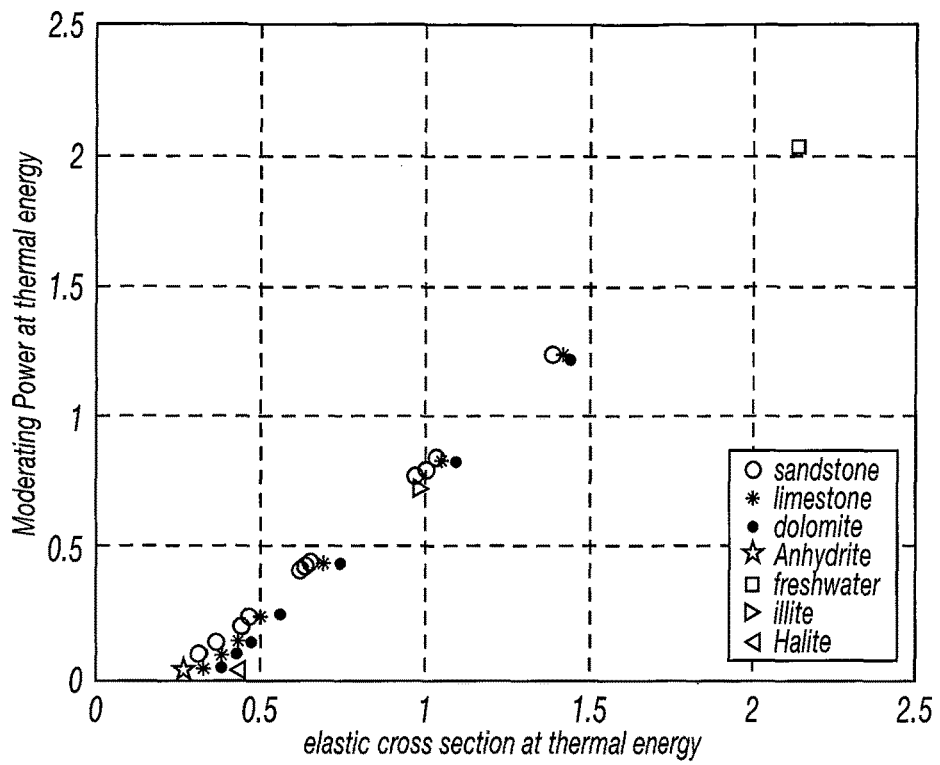
FIG. 4 shows a graph of moderating power (cm$^{-1}$) with respect to thermal neutron elastic scattering cross section (cm$^{-1}$).

FIG. 4 shows a graph of the correlation between the neutron elastic scattering cross section and the moderating power at thermal energy. There are many different formation conditions shown in FIG. 4, including rock mineralogy including sandstone, limestone, dolomite and various water filled porosities (0 percent porosity ("p.u.") to 100 p.u.), and some other lithologies like halite, illite and anhydrite. FIG. 4 shows a strong correlation between the moderating power and the elastic scattering cross section at thermal energy. However, not all the foregoing conditions fall precisely on the same line. For 0-p.u. sandstone, limestone, dolomite and halite, the moderation power and elastic cross section have slightly different behavior. It has been determined empirically that the elastic cross section is more accurate in predicting a neutron logging tool response than the moderating power. However, either of them may be used for purposes of methods according to the present disclosure.

Figure 5:
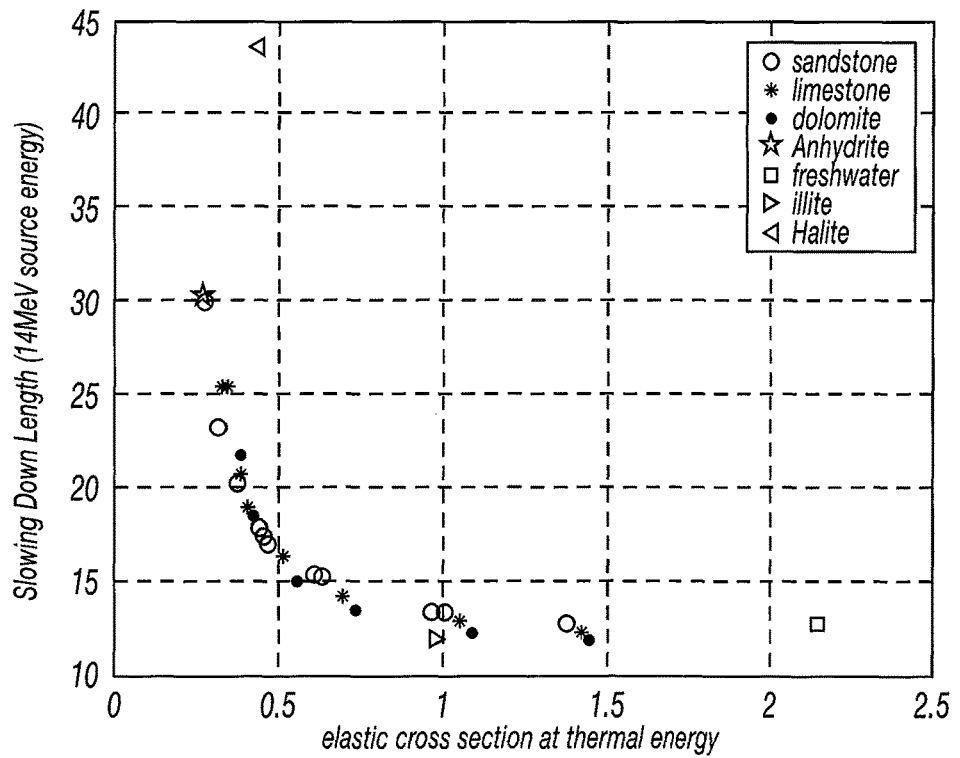
FIG. 5 shows a graph of neutron slowing down length (cm) vs. thermal neutron elastic scattering cross section (cm$^{-1}$).

FIG. 5 shows the correlation between the thermal neutron elastic scattering cross section and the neutron slowing down length (from 14 MeV down to thermal energy). One can use the elastic cross section to determine the slowing down length in most conditions based on the correlation shown in FIG. 5. There are several exceptional conditions. The computation of the slowing down length uses neutron capture cross section, which varies from 14 MeV to thermal energy, in addition to the elastic cross sections. The resonance integral is an important consideration in capturing a neutron during its slowing down. Sigma, which is the neutron capture cross section at the thermal energy, may or may not correlate with the resonance integral. However, one can still use sigma in addition to the elastic cross section to determine the slowing down length more accurately. The porosities in FIG. 5 are 0 p.u., 2.5 p.u., 5 p.u., 10 p.u., 20 p.u., 40 p.u., 60 p.u., and 100 p.u. Another exception is in the high porosity region (>40 p.u.). From 40 p.u. to 100 p.u., the slowing down length does not change much but the elastic cross section increases linearly as the porosity increases. This phenomenon may be described as the slowing down length saturating at high porosity. The porosity value at which saturation begins depends on the neutron source energy. With an AmBe neutron source with average emitted neutron energy around 4 MeV, the slowing down length does not saturate at high porosity. For the conversion of 14 MeV slowing down length to AmBe slowing down length the formation density can be used to help with the conversion as more fully described in U.S. Pat. No. 7,667,192 issued to Fricke et al. Thus, the use of the formation bulk density in addition to neutron cross sections can help to predict the neutron tool response more accurately, especially at high porosity.

A fast neutron measurement is possible based on fast neutron detectors. The energy of a fast neutron is typically in the MeV range. There are two ways in which to measure fast neutrons. One is the direct measurement, which uses a fast neutron detector; the other is an indirect measurement, which measures the fast neutron induced gamma rays. Fast neutrons can induce gamma rays through inelastic neutron scattering (n, n'y) or a neutron reaction such as (n, p) or (n, alpha), and other reactions which have an energy threshold for their production in the MeV range. Among all reaction types inducing gamma rays, the inelastic scattering is the predominant one. In principle, the fast neutron measurement measures how strongly the fast neutrons are attenuated by the formation. Beside the reactions that can induce gamma rays, elastic scattering can also attenuate fast neutrons. It can slow down fast neutrons or scatter them away. There are many choices of cross sections, which can be used to interpret a fast neutron measurement. One can choose to use the total, elastic, or inelastic cross sections, or any form of linear combination of the foregoing at the neutron source energy. Instead of using the cross section at a single energy level, one can use integrated cross sections over a certain neutron energy range. In this disclosure, the elastic cross section at the source energy may be used to demonstrate the example method.

Figure 6:
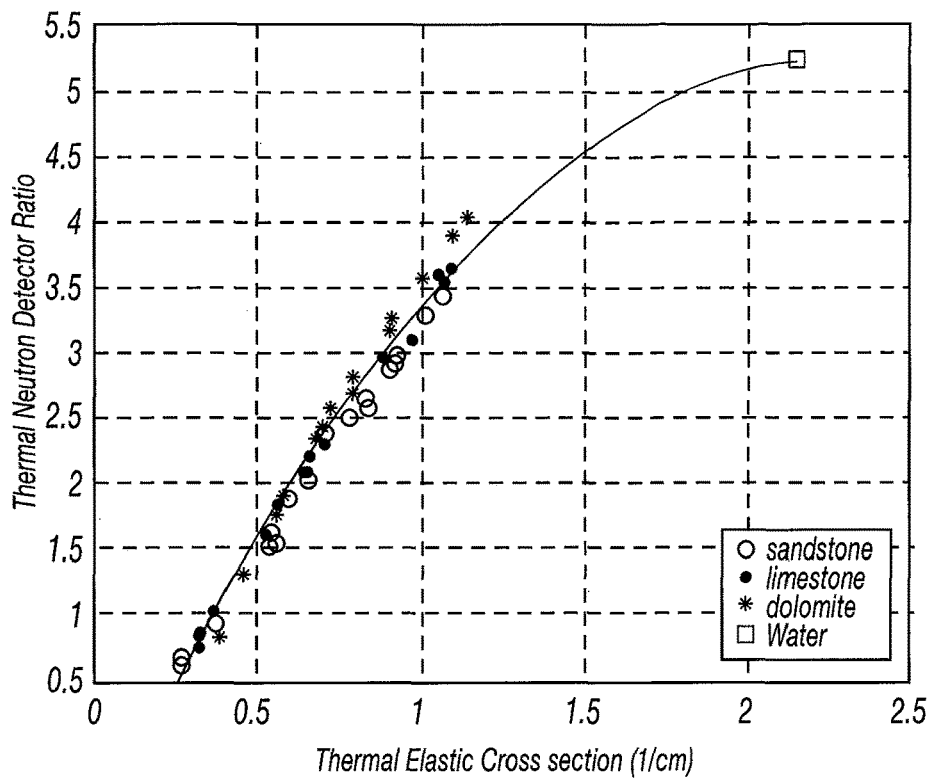
FIG. 6 shows a graph of CNT thermal neutron detector ratio as a function of the macroscopic thermal neutron elastic scattering cross section.

FIG. 6 shows the thermal neutron detector count rate ratios measured by a two-detector thermal neutron instrument using an AmBe radioisotope source. One example of such an instrument is sold under the trademark CNT, which is a trademark of Schlumberger Technology Corporation, Sugar Land, Tex. The CNT well logging tool for purposes of evaluating methods according to the present disclosure was operated in laboratory conditions including a number of different formation tanks, including three lithologies (sandstone, limestone and dolomite) with various fresh water filled porosities (from 0 p.u. to 100 p.u.). The solid line in FIG. 6 represents a polynomial fit through all the data points. The three different lithologies appear to be on the same curve. One may conclude that the thermal elastic cross section can represent what the tool measures independent of the lithology. In case of salty water filling the pore space of such formations, sigma measurements may be used additionally to predict the tool response. Sigma may be measured using many types of pulsed neutron logging instruments known in the art.

Figure 7:
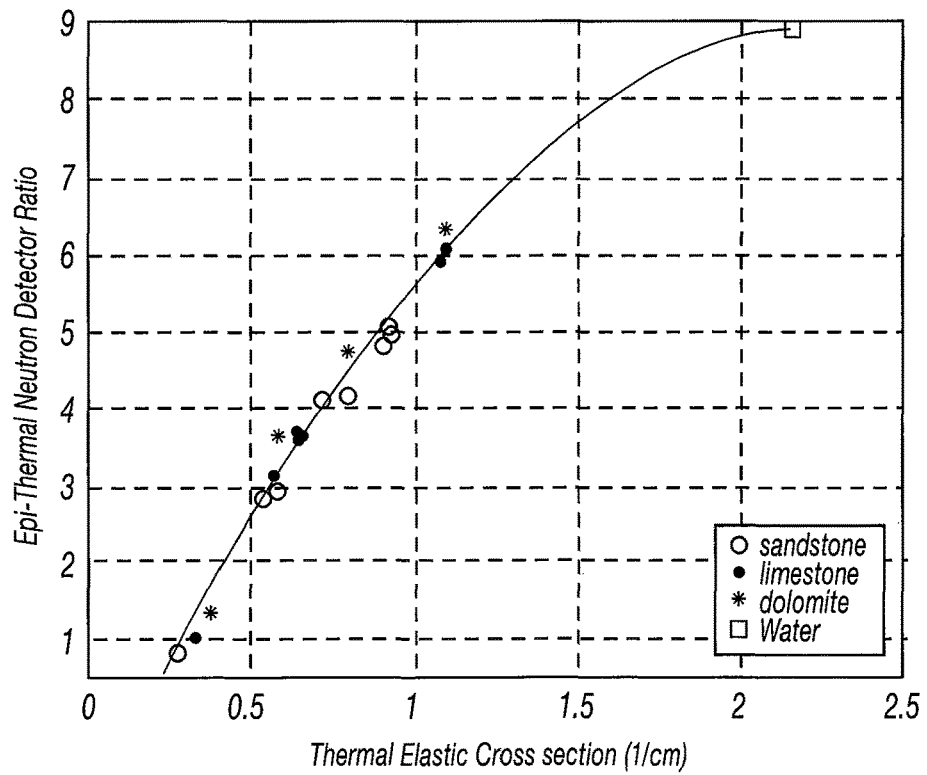
FIG. 7 shows a graph of CNT epithermal neutron detector ratio as a function of the macroscopic thermal neutron elastic scattering cross section.

FIG. 7 shows the epithermal neutron detector count rate ratios measured by a modified version of the CNT instrument in the laboratory as a function of the macroscopic thermal neutron elastic cross section. The modified CNT is equipped with a cadmium filter around the two neutron detectors to suppress detection of thermal neutrons and let substantially only epithermal neutrons pass through to the detectors. There may be a number of different formation tanks, including, e.g., three lithologies (sandstone, limestone and dolomite) with various fresh water filled porosities (from 0 p.u. to 100 p.u.). The solid line represents a polynomial fit through all the data points. Similar to the thermal ratio (FIG. 6), the count rate ratios for the three different lithologies stay on the same curve. Thus, the same principle can be applied to epithermal count rate ratios measured by such a well logging instrument. Another way to measure neutron porosity using an epithermal neutron detector is the slowing down time (SDT) measurement, which requires a pulsed neutron generator as a source and measuring an epithermal neutron count rate as a function of time (epithermal neutron die-away). The SDT measurement can also be interpreted using the macroscopic thermal neutron elastic cross section in a way similar to that discussed above. Sigma may (or may not) be used additional to the macroscopic thermal neutron elastic cross section to interpret the SDT measurement to improve the accuracy.

Figure 8:
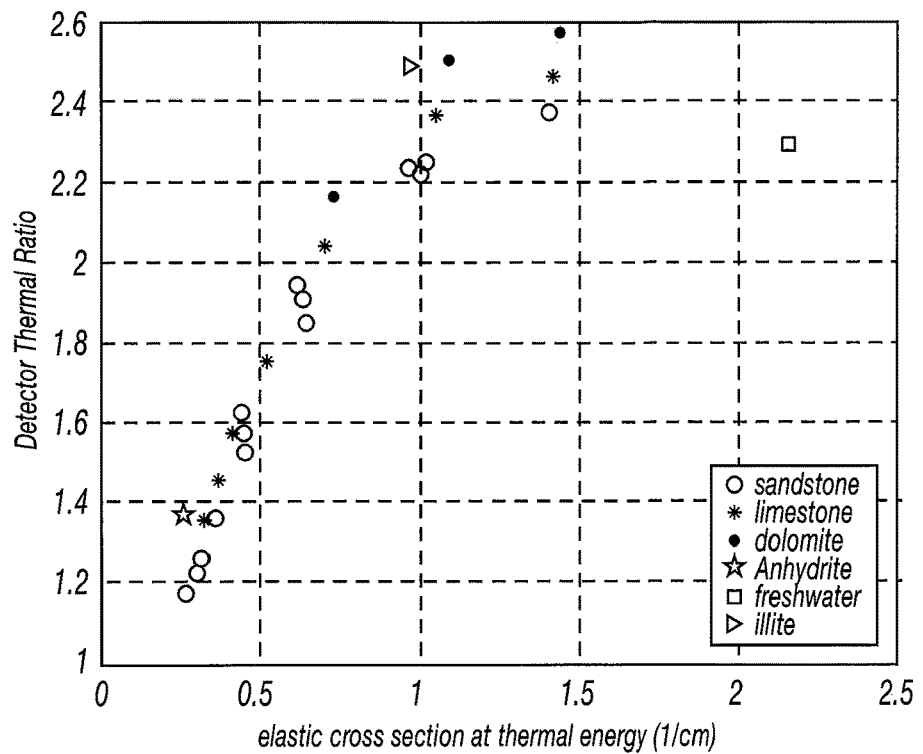
FIG. 8 shows a graph of pulsed neutron logging tool thermal detector ratio with respect to thermal neutron elastic scattering cross section.

FIG. 8 shows modeling results based on a pulsed neutron logging tool with two gamma ray detectors. The thermal neutron induced capture gamma rays are measured in the detectors after the end of each neutron burst. The ratios of the two detector count rates are plotted against the thermal neutron elastic cross section. The formation conditions include sandstone, limestone, dolomite with various fresh and salty water porosities (0, 2.5, 5, 10, 20, 40, 60, and 100 p.u.), 10-p.u. methane ($CH_4$) filled porous sandstone, 0-p.u. anhydrite, and illite. The wellbore condition is a fresh-water filled open hole (6-in bit size). At low porosity (cross section is lower than 0.5 l/cm), the three lithologies (sandstone, limestone, and dolomite) can all be described well by the thermal elastic cross section. Sigma and density measurements may be required to predict the instrument response in more complex conditions.

Figure 9:
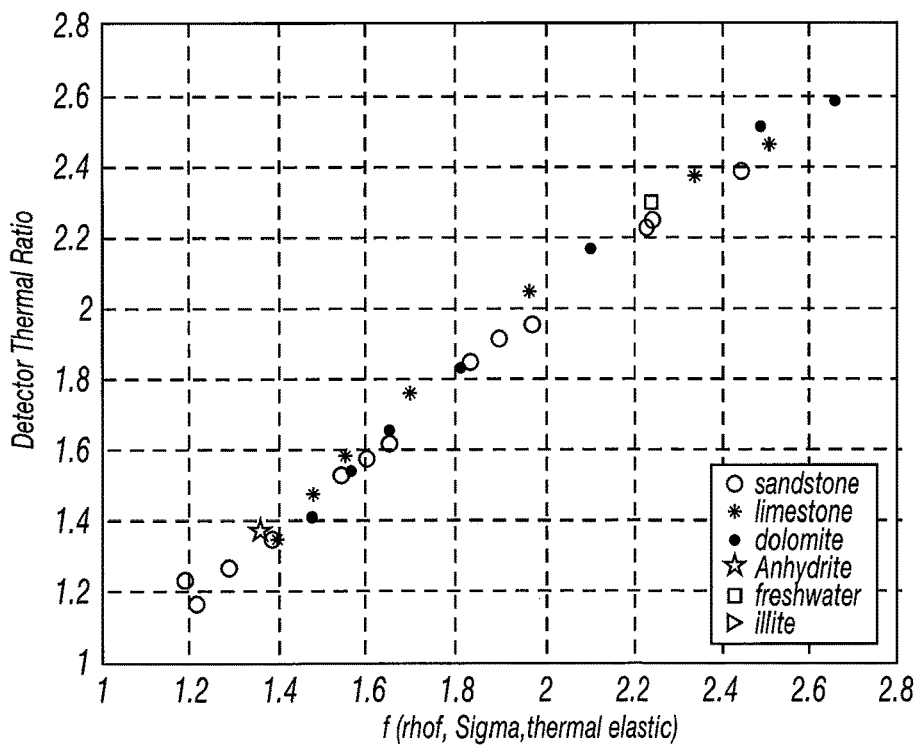
FIG. 9 shows a graph indicating how pulsed neutron logging tool detector thermal ratio can be predicted accurately by a function of thermal neutron elastic scattering cross section, bulk density and sigma.

The data points in FIG. 9 are taken at the same conditions as the ones in FIG. 8. A forward model has been developed to predict the detector ratios based on three formation quantities, bulk density, sigma and thermal elastic cross section. FIG. 9 shows the modeled detector count rate ratio versus the forward model prediction $f$. The predictions agree with the data very well. This forward model is a second order polynomial function of the foregoing three quantities. There are other possible formulas that can be used.

As a practical matter, bulk density and sigma can be measured using well known logging instruments. Thus, one can derive the formation thermal elastic cross section from any neutron porosity tool. Then one may derive the porosity or saturation from it, in a manner similar to that used with bulk density measurements.

Figure 10:
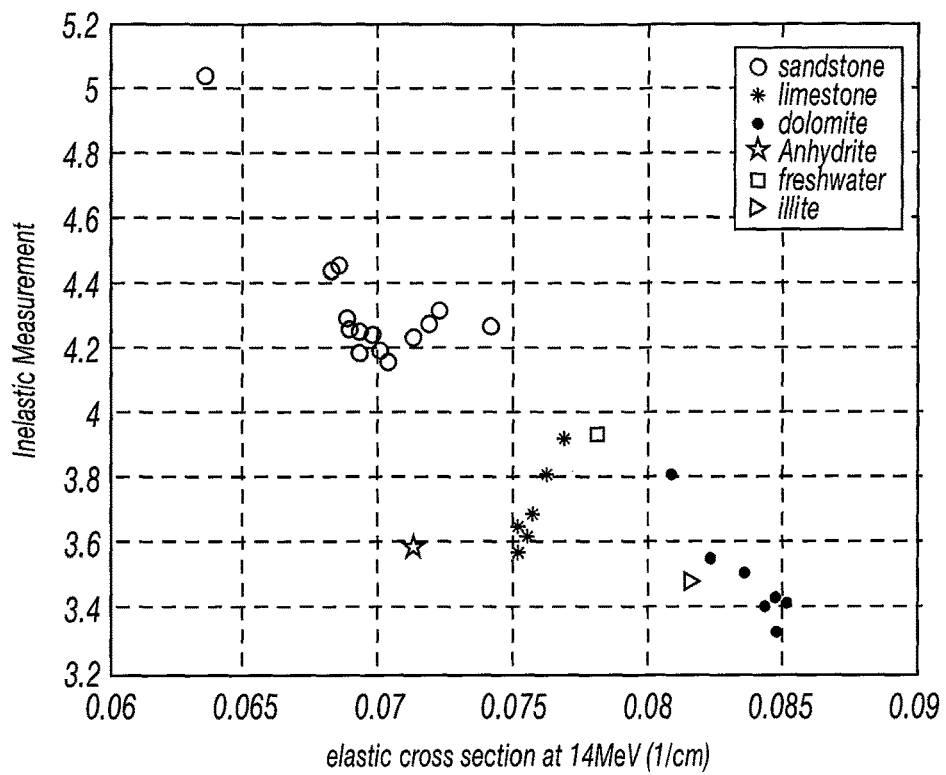
FIG. 10 shows a graph of pulsed neutron logging instrument inelastic measurement with respect to 14 MeV neutron elastic scattering cross section.

The data points in FIG. 10 are taken at the same conditions as the ones in FIG. 8. The y-axis in FIG. 10 is an inelastic gamma ray measurement, which is obtained using a pulsed neutron well logging tool having a 14-MeV source and a gamma ray detector. The measurement is essentially the inelastic gamma ray (fast neutron induced gamma rays from inelastic scattering) count rate measured in the detector. It can be obtained by removing the capture gamma ray (thermal neutron induced gamma rays from capture) count rate from the gamma ray count rate measured during the source neutron burst, which contains both inelastic and capture gamma rays. There are other ways to obtain an inelastic measurement known in the art. The y-axis in FIG. 10 is this inelastic measurement divided by a neutron output measurement from a fast neutron monitor to remove the neutron generator output variation. Since only fast neutrons with energy above a certain threshold (typically above the 1-MeV level) can induce a gamma ray inelastically, theoretically an inelastic measurement is only sensitive to fast neutrons with energy approximately in the 1 MeV and above range. The x-axis in FIG. 10 is the neutron elastic cross section at 14 MeV, which is the neutron source energy of a d-T generator. The inelastic measurement is more sensitive to gas-filled porosity than to water-filled porosity. The highest value in the inelastic measurement corresponds to 10 p.u. $CH_4$ (density 0.15 g/cm$^3$)-filled sandstone. The inelastic measurement also has a lithology dependence: sandstone is higher than limestone, which is higher than dolomite. The 14-MeV elastic cross section describes qualitatively the behavior of the inelastic measurement. Other formation quantities, such as bulk density, may be required to predict the inelastic response more accurately, as in the example shown below.

The inelastic gamma ray measurement discussed above is based on a single detector with a pulsed neutron generator as a source. As a practical matter, the output of a pulsed neutron generator can vary over time. Thus, the single detector measurement may need to be normalized (e.g., divided by) a neutron generator output measurement in a real time to be free of neutron output variation. Such a neutron output measurement can be obtained directly using a fast neutron detector located with respect to the neutron generator so as to have response substantially only related to generator output, or indirectly from the neutron generator operation parameters.

Figure 11:
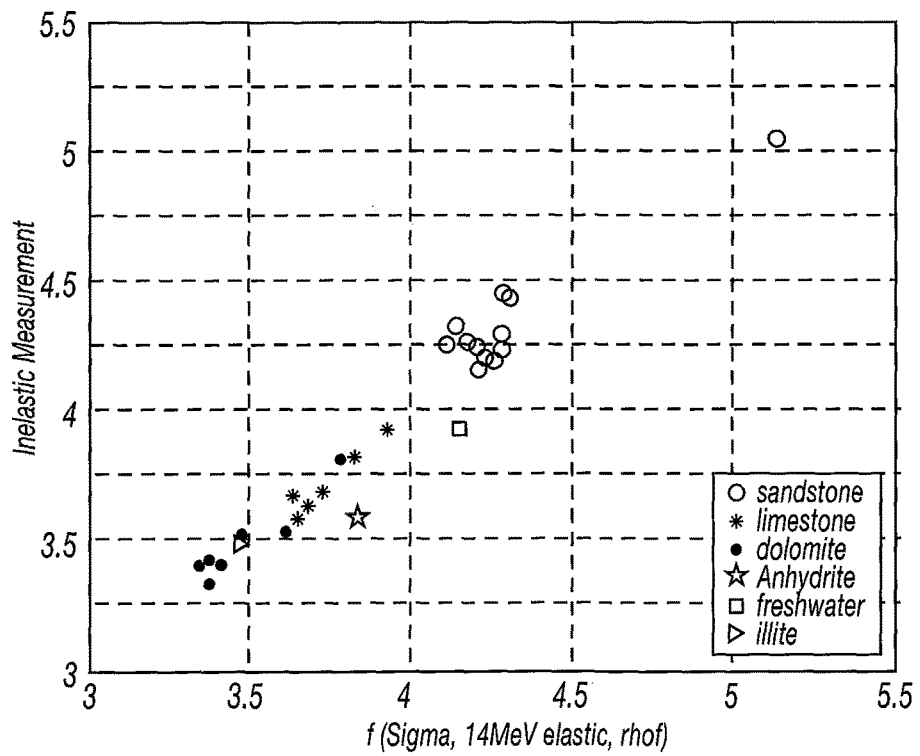
FIG. 11 shows a graph of how pulsed neutron logging tool inelastic measurements can be predicted accurately by a function of the 14 MeV neutron elastic scattering cross section, bulk density and sigma.

The data points in FIG. 11 are taken at the same conditions as the ones in FIG. 8. A forward model has been developed to predict the inelastic measurement count rate based on three formation quantities, sigma, 14-MeV elastic cross section and bulk density. FIG. 11 shows the inelastic measurement versus the forward model prediction. The formula is a second order polynomial of the foregoing three formation quantities. The prediction is quite accurate. The 0-p.u. anhydrite and 100-p.u. water predictions are less precise than other formation conditions. Sigma and bulk density may be measured using well known logging instruments as explained above. When such measurements are available, one can derive the 14 MeV elastic cross section from a pulsed neutron tool. Depending on the application, one can use other formulas to predict the tool response. One can also choose not to use the bulk density but only sigma and the 14-MeV elastic cross section to predict the tool response (albeit with somewhat reduced accuracy).

TABLE 1

Neutron cross section values of a few typical formation matrix materials and formation fluids

| Material | Macroscopic neutron elastic scattering cross section at thermal energy (1/cm) | Macroscopic neutron elastic scattering cross section at 14-MeV energy (1/cm) |
| --- | --- | --- |
| Sandstone | 0.2651 | 0.0684 |
| Limestone | 0.3242 | 0.0751 |
| Dolomite | 0.3762 | 0.0851 |
| Fresh Water | 2.1478 | 0.0780 |
| CH4 (0.15 g/cm3) | 0.7066 | 0.0201 |
| Diesel | 2.3296 | 0.0785 |
| Wet Illite | 0.9516 | 0.0802 |

Table 1 lists neutron elastic scattering cross sections of some typical formation matrix materials and fluids. In terms of thermal elastic cross sections, the three principal matrix materials (lithologies) have different values but are generally within a small range, while the values of water and oil are similar and substantially higher than the three lithologies. The values of gas and clay are higher than the three lithology values but lower than water and oil due to the difference in hydrogen content. Thus, the thermal elastic scattering cross section is a measurement, which is very sensitive to the presence of water or oil, may not be able to differentiate water from oil, has different lithology effects, and is sensitive to gas and clay. The thermal elastic scattering cross section has a different interpretation than other well-known neutron porosity measurements.

The 14-MeV elastic scattering cross section is a quantity which is not known to be used in the petroleum industry. The values for the three clean lithologies, fresh water, oil, and clay are different but very similar. The only outlier is gas, which is factor 3 to 4 times smaller than the others. Thus, this quantity is very sensitive to the presence of gas in the formation, and still has a small lithology and water-filled porosity effect. This measurement can be used to quantify gas-filled porosity and gas-saturation.

After extracting the neutron elastic cross sections at thermal energy and 14-MeV energy from a neutron logging tool, one can use one of them (or both) to solve for petrophysical parameters such as porosity, fluid saturation, and so on. In the meantime, one can also combine the two newly defined neutron cross sections with other measurements, such as bulk density, sigma, natural gamma ray, resistivity, and so on to solve more complex problems.

Below are examples of applications based on the two above defined neutron cross sections. A well logging instrument, such as explained with reference to FIG. 1D may emit neutrons (at least 1 MeV) into formations surrounding a wellbore. Radiation events, such as inelastic gamma rays, fast neutrons, epithermal neutrons, thermal neutrons and capture gamma rays may be measured at at least two different longitudinal distances from the point of neutron emission. For example, if thermal neutrons or epithermal neutrons are detected, a measured count rate or a ratio of two measured count rates taken from detectors at different spacings from the source may be used to determine the thermal neutron elastic scattering cross-section. If high energy neutrons or resulting gamma rays are detected, a measured count rate or a ratio of two measured count rates as above may be used, in some examples in combination with a measurement of bulk density or sigma, to determine the high energy neutron elastic scattering cross-section. A pulsed neutron instrument with suitable detectors may be used in some examples of the foregoing, to determine the high energy neutron elastic scattering cross section and sigma (by detecting thermal neutron capture gamma rays or thermal neutrons).

The formation typically contains the rock matrix and pore space, which can be filled with fluid (oil, water, or salty water) or gas, or a mix of them. The formation cross section $\Sigma_{total}$ can be written as indicated in Eq. 6, Eq. 7 or Eq. 8 shown below depending on the available knowledge or assumptions. This is very similar to any derivation of a petrophysical property that follows a known mixing law, e.g., a linear volumetric mixing law. In the present disclosure are introduced two independent neutron cross sections, which are the thermal neutron elastic scattering cross section and the 14-MeV neutron elastic scattering cross section.

Depending on the logging tool used, different neutron cross sections can be measured. For example, the CNT (compensated neutron tool) well logging instrument cannot measure sigma or the 14-MeV neutron elastic cross section, but may be able to measure the thermal neutron elastic scattering cross section. Pulsed neutron logging tools known in the art may be able to measure both the 14-MeV elastic scattering cross section, thermal scattering cross section and sigma.

Depending on the existing knowledge or user assumptions, users can input the matrix cross section $\Sigma_{matrix}$ and fluid cross section $\Sigma_{fluid}$, then solve for the porosity $\Phi$ from the measured total cross section $\Sigma_{total}$ as indicated in Eq. 6.

The user can input a value for gas cross section $\Sigma_{gas}$ additionally then to solve for both porosity $\Phi$ and gas saturation $S_{gas}$ based on Eq. 7. In this case, the user needs two independent measurements because there are two unknowns. At least one of the two independent measurements is one of the two neutron cross sections. Others can be another neutron cross section or another type of measurement, such as density, sigma, natural gamma ray, resistivity, and so on.

Additionally, the user can input the oil cross section to solve for porosity $\Phi$, gas saturation $S_{gas}$ and oil saturation $S_{oil}$ based on Eq. 8. In this case, the user needs three independent measurements because there are three unknowns. At least one of the three independent measurements is one of the two neutron cross sections. The others can be the other neutron cross sections or another type of measurement, such as density, sigma, natural gamma ray, resistivity, and so on.

Of note is that Eq. 6, Eq. 7, and Eq. 8 are all linear functions of the volume fraction (porosity or saturation). This makes problem solving very easy and flexible.

$$\Sigma_{total} = (1-\phi) \cdot \Sigma_{matrix} + \phi \cdot \Sigma_{fluid} \quad (6)$$

$$\Sigma_{total}(1-\phi) \cdot \Sigma_{matrix} + \phi \cdot (1-S_{gas}) \cdot \Sigma_{fluid} + \phi \cdot S_{gas} \cdot \Sigma_{gas} \quad (7)$$

$$\Sigma_{total}(1-\phi) \cdot \Sigma_{matrix} + \phi \cdot (1-S_{gas}-S_{oil}) \cdot \Sigma_{water} + \phi \cdot S_{gas} \cdot \Sigma_{gas} + \phi \cdot S_{oil} \cdot \Sigma_{oil} \quad (8)$$

Following the same principle, other applications may be based on one (or both) of the two measured neutron cross sections.

In another embodiments, a new term may be introduced called TNXS, which stands for thermal neutron cross section. TNXS may be equal to the neutron elastic scattering cross section at thermal energy or at epithermal energy, as explained with reference to the previous embodiments. However, TNXS may also be defined as a weighted linear combination of the thermal neutron elastic scattering cross section and any other formation bulk property, for example and without limitation, bulk density, thermal neutron capture cross-section (Sigma), atom density, macroscopic elastic scattering cross section at 1 eV, moderating power (as described with reference to the previous embodiments). The purpose of introducing the term TNXS is to improve the accuracy of using determined neutron cross sections to predict neutron porosity. Using the thermal neutron cross section alone to predict neutron porosity is only a first order approximation.

Because TNXS is a linear combination of a number of formation bulk properties that follow a volumetric mixing law, TNXS follows the volumetric mixing law as well. TNXS may be used with other available formation parameter measurements such as bulk density and/or Sigma to predict formation properties such as neutron porosity. If bulk density and/or Sigma are available, the value of TNXS can be extracted from the measurements. For example, the detector count rate ratio from the compensated neutron tool measurement (TNRA) can be written as a function of TNXS, bulk density and Sigma as indicated in Eq. (9), which represents a possible forward model of the measured quantity TNRA. The foregoing specific formation parameters used to estimate TNXS are not limiting; they may be convenient because they may be determined using measurements from certain types of multiple detector pulsed neutron well logging instruments, thus simplifying the instrumentation needed to determined TNXS.

Figure 12:
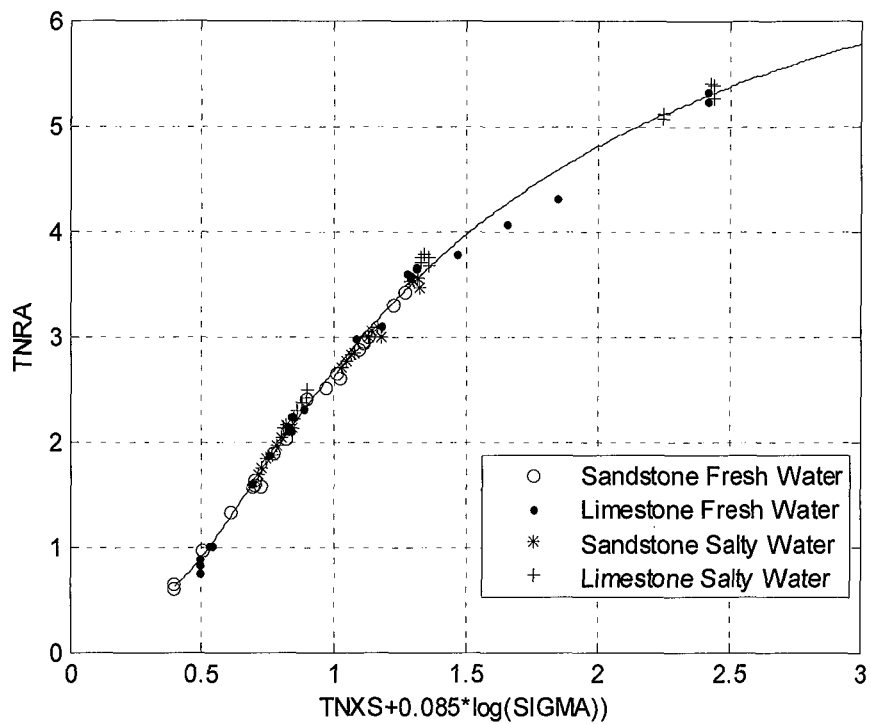
FIG. 12 shows a graph of modeled thermal neutron detector count rate ratio measured in a conventional, open hole compensated neutron porosity tool at laboratory conditions as a function of the parameter TNXS with a correction for thermal neutron capture cross section, Sigma.

The formula to determine TNXS is not limited to linear combinations. In the example shown graphically in FIG. 12 the relationship may be a function fitted to data. The function is shown as Eq. (9), and TNXS in this example is defined as the thermal elastic scattering cross section.

$$TNRA = \exp\left[a_1 \cdot \left(\frac{1}{TNXS + 0.085 \cdot \log(\text{Sigma})}\right)^3 + a_2 \cdot \left(\frac{1}{TNXS + 0.085 \cdot \log(\text{Sigma})}\right)^2 + a_3 \cdot \left(\frac{1}{TNXS + 0.085 \cdot \log(\text{Sigma})}\right) + a_4\right] \quad (9)$$

In describing the previous embodiments, it was shown that the net inelastic gamma ray measurement from a pulsed neutron logging instrument may be predicted mainly by the elastic scattering cross section at the source energy (which may be 14 MeV but is not so limited). Similarly to the introduction of the term TNXS, in the present embodiment a new term called FNXS may be introduced. FNXS represents the fast neutron cross section. FNXS may be defined as a weighted linear combination of the elastic scattering cross section at the neutron source energy (e.g., 14 MeV) with any other formation bulk properties, including for example and without limitation, formation bulk density, Sigma, atom density, macroscopic inelastic scattering cross section at a particular neutron energy or integrated over a particular neutron energy range. The purpose of introducing the FNXS term is to improve the accuracy of using the high energy neutron cross section to predict the fast neutron measurement. Using the neutron source energy (e.g., 14 MeV) elastic neutron cross section alone to predict the results of the fast neutron measurement is only a first order approximation.

Figure 13:
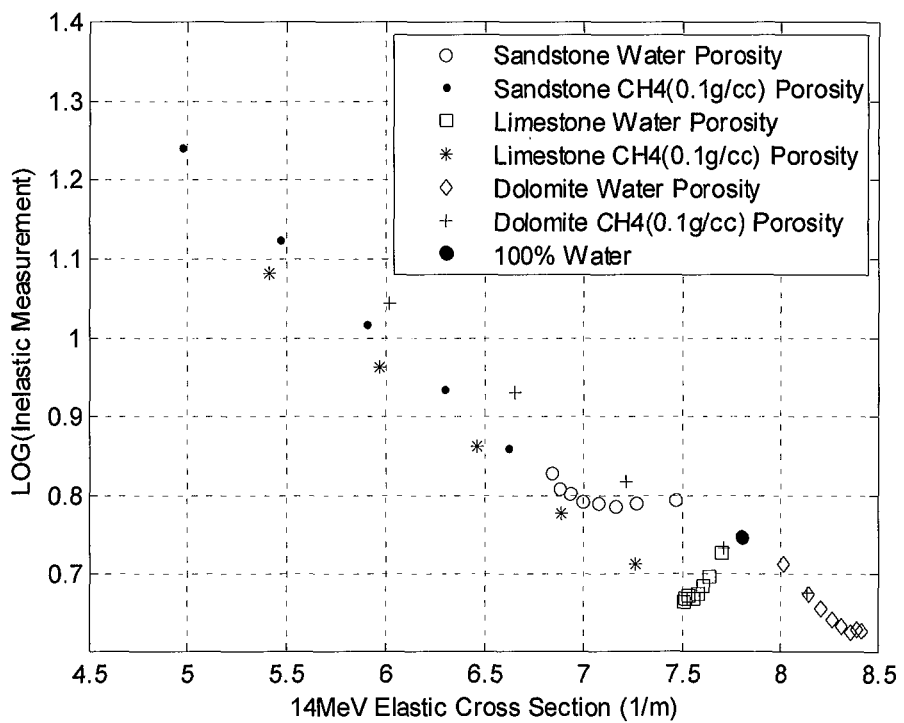
FIG. 13 shows a graph of modeled inelastic gamma ray events in a gamma ray detector of a typical pulsed neutron well logging instrument as a function of the 14-MeV neutron macroscopic elastic scattering cross section.
Figure 14:
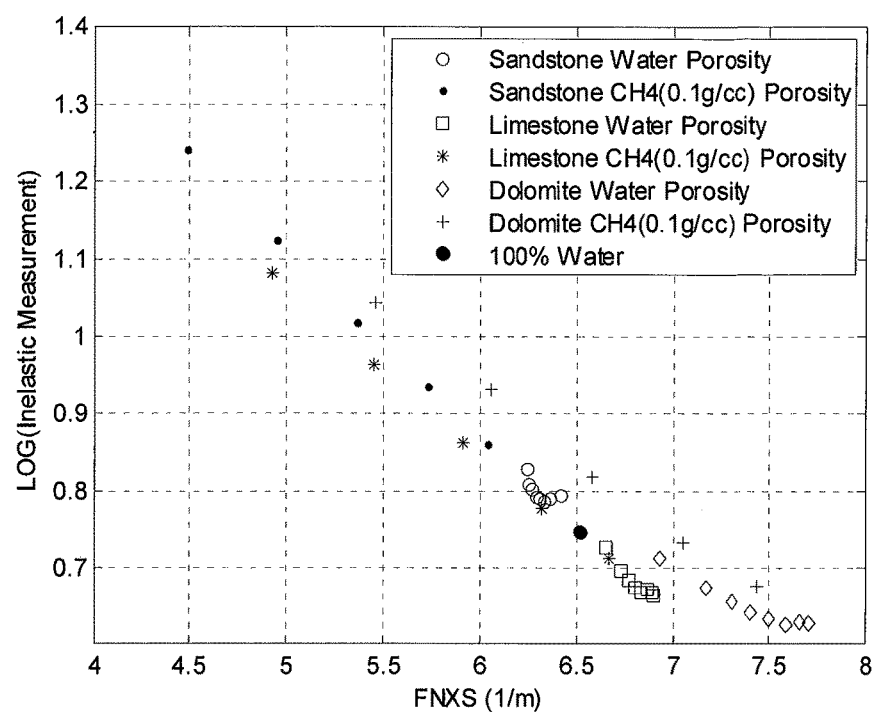
FIG. 14 shows a graph of modeled inelastic gamma ray events in a gamma ray detector of a typical pulsed neutron logging tool as a function of the parameter FNXS.

FIG. 13 and FIG. 14 show an example for FNXS. FIG. 13 shows the logarithm of modeled inelastic gamma ray count rate as a function of the 14-MeV macroscopic elastic scattering cross section for various formation conditions. FIG. 13 shows modeled inelastic gamma ray events in a gamma ray detector of a typical pulsed neutron logging instrument as a function of the 14-MeV neutron macroscopic elastic scattering cross section. The water-filled porosities are 0, 4, 10, 17, 25, 34, 45 and 65 p.u., and methane gas (0.1 g/cm$^3$) filled porosities are 0, 4, 10, 17, 25 and 34 p.u. As can be observed in FIG. 13, the 14-MeV cross section dominates the inelastic measurement, but it is only a first order approximation with limitations.

FIG. 14 shows the same modeled data plotted as a function of FNXS, which is defined by Eq. (10). Essentially, in this case, FNXS is defined as a weighted linear combination of the 14-MeV elastic cross section, the 14-MeV inelastic cross section, and the atom density. Compared to the results shown in FIG. 13, using FNXS may improve the prediction accuracy, i.e., the accuracy of the forward model.

$$FNXS = \Sigma_{@14\ MeV}^{elastic} + a_1 \cdot \Sigma_{@14\ MeV}^{inelastic} + a_2 \cdot \rho_{atom} \quad (10)$$

The approach used in Eq. (10) is to determine an expression for a quantity, herein referred to as the effective fast neutron cross section, which is a linear combination of the volume fractions of each of the materials in the formation including the fluid, for which the net inelastic count rate is a function of that quantity only. As is well known, neutron energy loss due to inelastic reactions is much more complicated than the elastic case both because the cross sections can vary dramatically with energy as can the energy loss per interaction. Rather than estimating the effective fast neutron cross section by using density and cross sections selected at a particular energy, an alternate approach is to derive the best effective fast neutron cross section for each material by optimizing these cross sections to fit the modeled and/or measured count rates over a data set containing the materials of interest. In particular let:

$c_i$=Net inelastic count rate at a given neutron output for a formation case i
$\rho_{ij}$=Atom number density of element j in formation case i
$FNXS_i$=Effective macroscopic fast neutron cross section for formation case i
$a_j$=Effective microscopic fast neutron cross section for element j
$f(FNXS)$=a function that provides the net inelastic count rate given the effective fast neutron cross section, e.g.

$$c = f(FNXS) = b \cdot e^{a \cdot FNXS} \quad (11)$$

By using the definitions of macroscopic and microscopic cross section, one may obtain the expression $$FNXS_i = \sum_j \rho_{ij} \cdot a_j \quad (12)$$

where $a_j$ (and hence $FNXS_i$) may be determined by modeling or measuring a preferably wide range of formation cases incorporating the minerals and fluids (and hence elements) commonly found in oil well logging and minimizing a cost function expression such as $$\sum_i (c_i - f(FNXS_i))^2 \quad (13)$$

Once the effective microscopic fast neutron cross section is obtained for common elements in earth, it is possible to compute the effective macroscopic fast neutron cross section FNXS for various formation using Eq. (13). Since the atom number densities are known functions of the material volume fractions alone, Eq. (5) satisfies the linear combination requirement of the approach noted above and by construction it may be the most desirable approach given the limitations of using a linear model.

Eqs. (6), (7), and (8) can be generalized as shown in Eq. (14).

$$\Sigma = \sum_{i=1}^{N} V_i \cdot \Sigma_i \quad (14)$$

Where Σ is a measured formation bulk quantity, which can be FNXS, TNXS, Sigma, bulk density, elemental yields, TOC, among other quantities. The formation can be divided into several parts with the total number equal to N. For examples, one can divide a formation into two parts: rock mineral grains (matrix) and fluid-filled pore space with N=2, as shown in Eq. (6). One can also divide a formation into three parts: rock matrix, fluid-filled pore space, and gas-filled pore space, with N=3, as shown in Eq. (7). One can divide formation to four parts: rock matrix, water-filled pore, oil-filled pore and gas-filled pore with N=4, as shown in Eq. (8). In above examples, one can also divide rock matrix further into several minerals such as sandstone, limestone, dolomite, shale, and so on. The fractional volume of each of the parts of the formation is defined as Vi in Eq. (14), and is the unknown to solve. The sum of the fractional volume is equal to 1 by definition as shown in Eq. (15). Σi is the bulk quantity of each part of the formation, which are typically available and computed from theoretical values.

$$1 = \sum_{i=1}^{N} V_i \qquad (15)$$

Eqs. (14) and (15) are linear equations for unknown variables Vi, thus they can be solved using simple linear algebra or any available linear solver application. If for example, FNXS, TNXS, and Sigma are measured and available, one can obtain 3 equations (one Eq. (14) for each measured bulk quantity). Thus, there are 4 equations available including Eq. (15). Thus as many as 4 unknown volumes can be solved, which means N≤4. In this case, one can solve the volumes of, for example quartz matrix, shale, fresh water, and gas. The total porosity can be determined to be equal to the sum of the volumes of fresh water and gas. The gas saturation can be determined to be equal to the volume of gas divided by the total porosity.

In other examples, one can add one or more of the following: condensate gas, $CO_2$ gas, steam, air, light oil, kerogen, into the linear model and solve the corresponding volumes using measured TNXS and/or FNXS with other measured bulk quantities.

Figure 15:
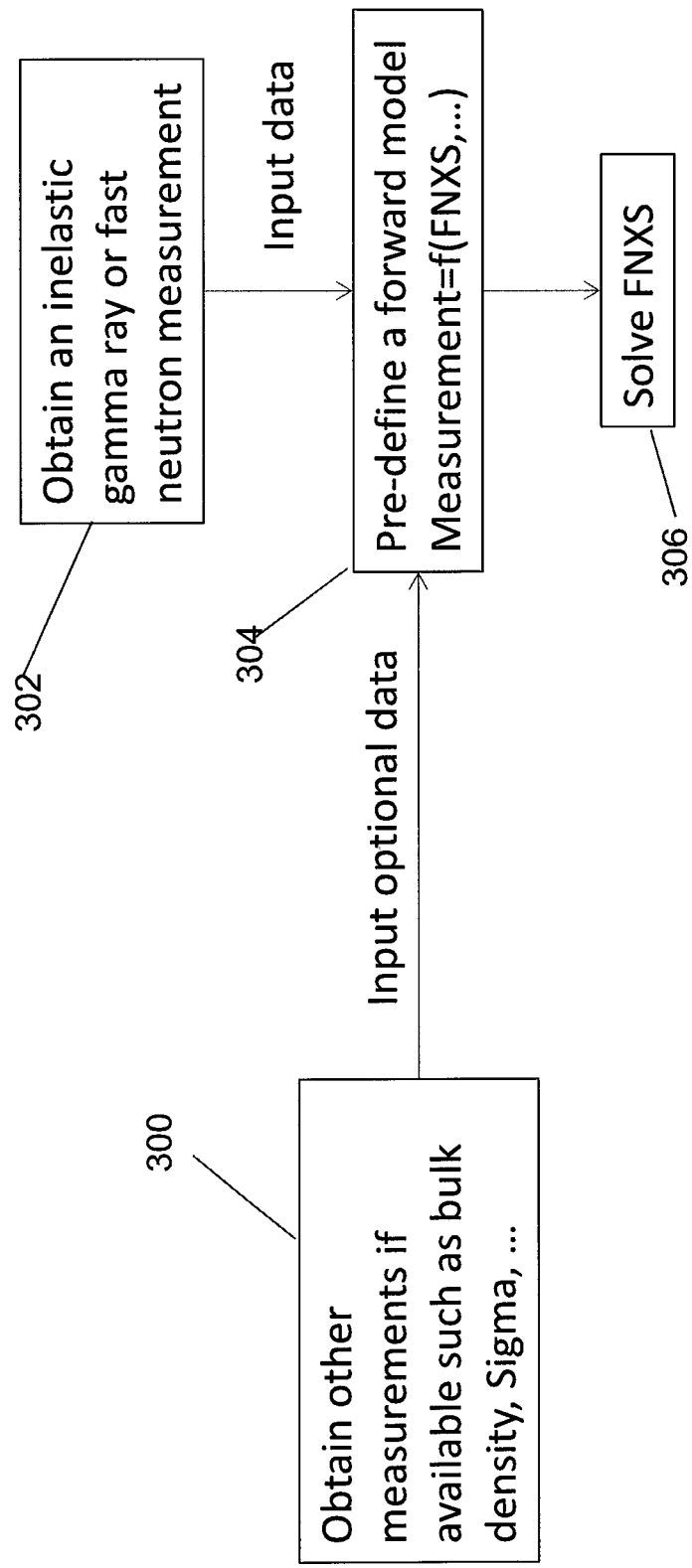
FIG. 15 shows a flow chart of an example process to obtain FNXS.

FIG. 15 shows a flow chart of an example technique for determining FNXS. At 302, inelastic gamma ray measurements may be made at one or more spaced apart locations from a neutron source, e.g., a pulsed neutron source as shown in FIG. 1A. At 300, other formation parameter measurements may be obtained, for example and without limitation, bulk density and Sigma. At 304, a forward model may be defined, such as explained with reference to Eq. (11). A value of FNXS may be determined, at 306, from the defined relationship at 304.

Figure 16:
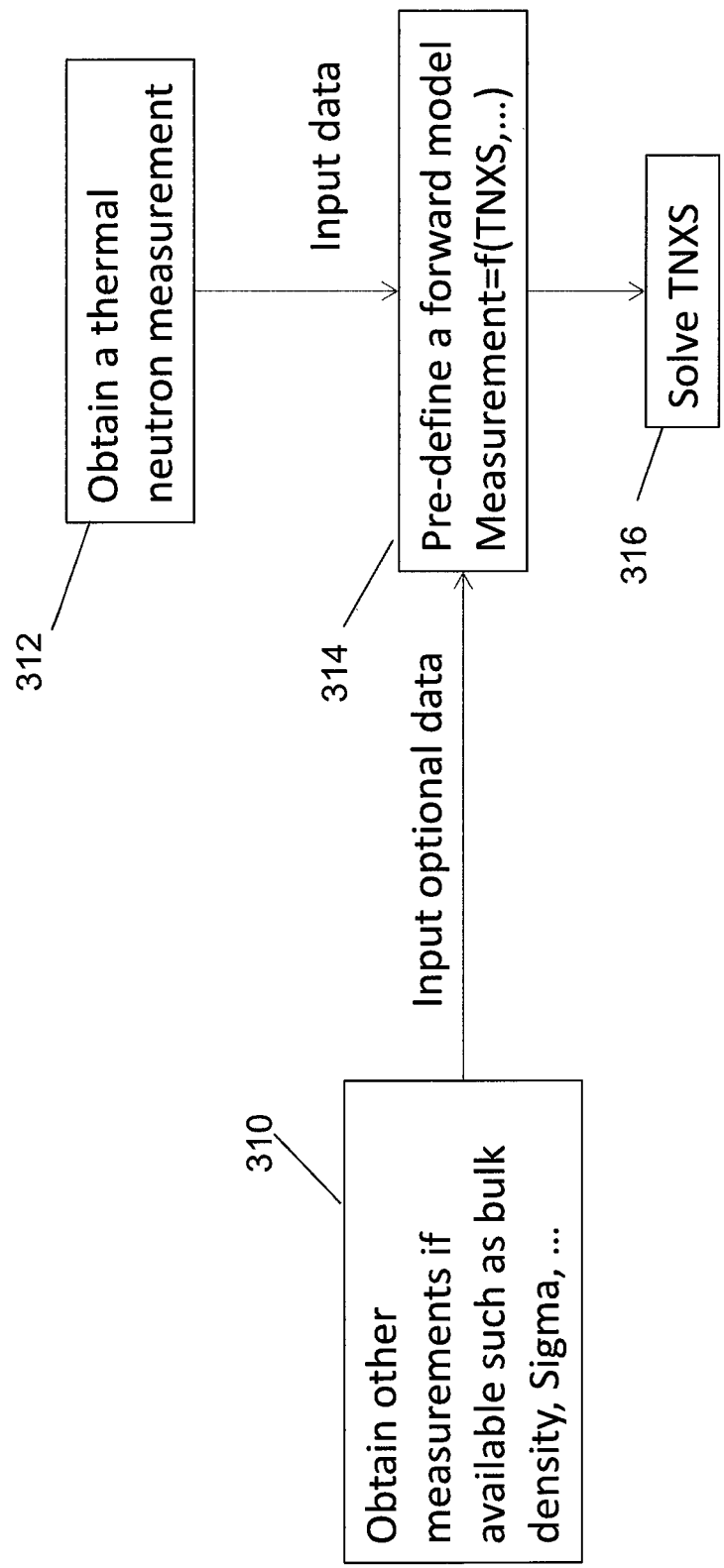
FIG. 16 shows a flow chart of an example process to obtain TNXS.

FIG. 16 shows a flow chart of an example technique for determining TNXS. At 310, formation parameter measurements, including without limitation bulk density and Sigma may be obtained. At 312, thermal neutron measurements, such as made by detecting capture gamma rays (see FIG. 1A) at two or more spaced apart locations from the neutron source may be obtained. At 314, the thermal neutron measurements and formation parameter measurements may be entered into an empirically determined relationship for TNXS with reference to the thermal neutron measurements and the formation parameter measurements as shown in Eq. (9). TNXS may be determined from the defined relationship at 316.

Figure 17:
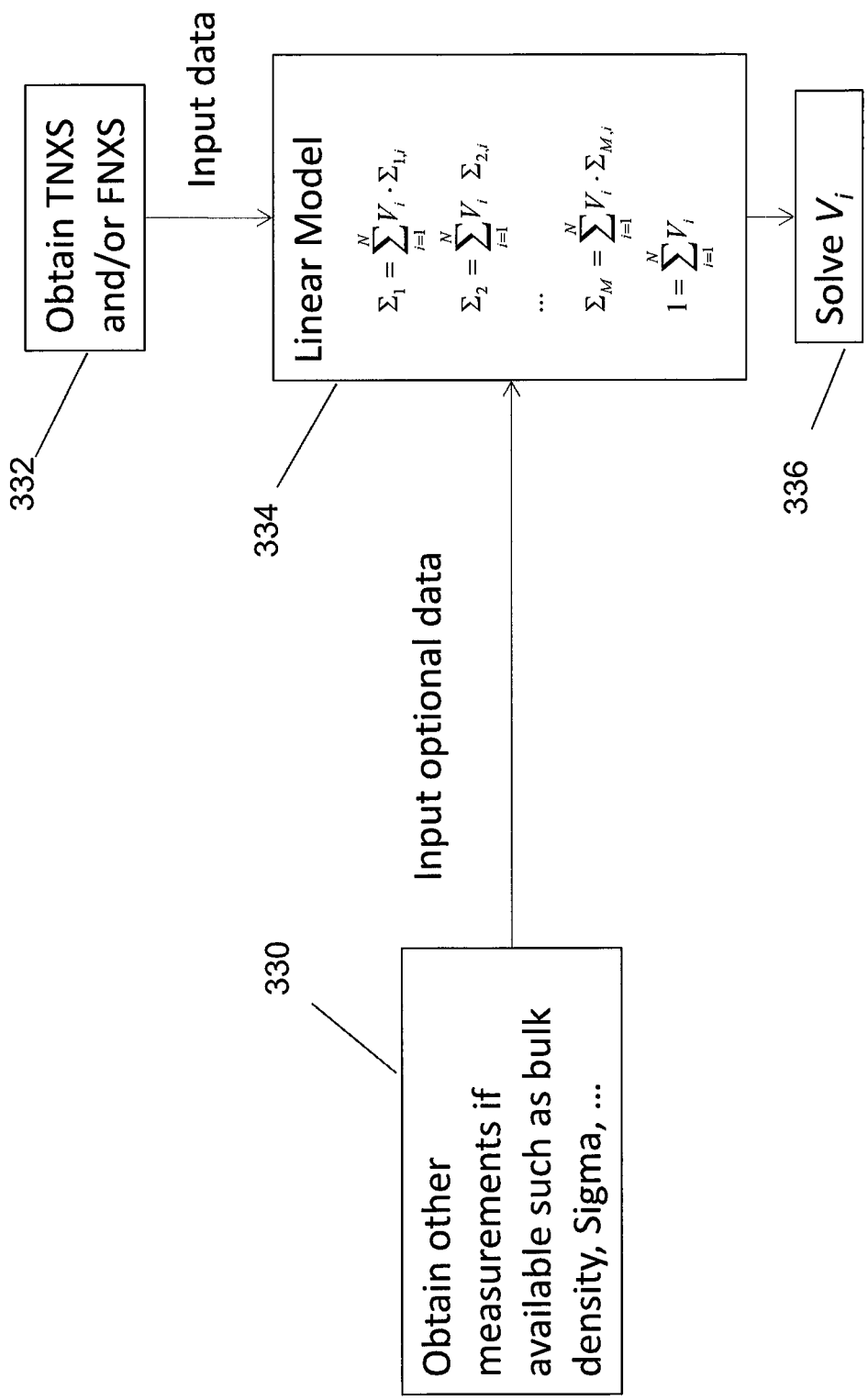
FIG. 17 shows a flow chart of an example process to determine formation parameters using FNXS or TNXS.

FIG. 17 shows a flow chart of using either FNXS or TNXS to determine formation porosity and content of the porosity. At 330, formation parameter measurements including but not limited to bulk density and Sigma may be obtained. At 332, either FNXS or TNXS obtained as explained with reference to FIGS. 15 and 16, respectively, may be obtained. At 334 TNXS or FNXS or both, may be entered into a volumetric calculation comprising a system of linear equations based on Eqs. (14) and (15). Solution to the system of linear equations enables determining volumes of each separate formation component, at 336, and as explained above with reference to Eqs. (14) and (15). In some embodiments, if both FNXS and TNXS are used, a volume fraction of at least one formation component may be determined without the need to use an additional measurement of a formation parameter.

A possible benefit of using bulk density and/or Sigma for the additional petrophysical parameter measurements is that such measurements may be obtained by using an instrument such as shown in and explained with reference to FIG. 1D. It will be appreciated by those skilled in the art that the processes described with reference to FIGS. 15, 16 and 17 may be performed in a computer system such as the one explained with reference to FIG. 1C, or in the recording unit shown at 70 in FIG. 1A or the recording unit shown at 250 in FIG. 1B.

Methods according to the present disclosure may enable determining formation properties such as porosity and fluid content in the rock pore spaces with more accuracy and less computational cost than prior methods using pulsed neutron measurements.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system, comprising:
   a well logging instrument comprising a neutron source configured to emit neutrons and at least one radiation detector spaced apart from the source along the instrument; and
   a processor that is coupled to the well logging instrument and is configured to receive a number of detected radiation events, resulting from imparting neutrons emitted from the neutron source into a formation at an energy level of at least 1 million electron volts (MeV), and determine a fractional volume of at least one component of the formation, the detected radiation events corresponding to fast neutrons and at least one of thermal or epithermal energy neutrons, wherein the processor is configured to perform at least one of
   (i) breaking down a fast neutron cross-section determined from the detected radiation events into a first plurality of fractional contributions and breaking down a thermal neutron cross-section determined from the detected radiation events into a second plurality of fractional contributions to determine the fractional volume of the at least one component of the formation, wherein the fractional volume is determined based at least in part on a system of equations comprising the first plurality of fractional contributions and the second plurality of fractional contributions, wherein the first plurality of fractional contributions comprises a first plurality of fractional volumes, wherein the sum of the first plurality of fractional volumes is one, wherein the second plurality of fractional contributions comprises a second plurality of fractional volumes, wherein the sum of the second plurality of fractional volumes is one; and (ii) receiving a measurement of at least one petrophysical parameter and breaking down the measurement of the at least one petrophysical parameter into a third plurality of fractional contributions and breaking down only the fast neutron cross-section into the first plurality of fractional contributions to determine the fractional volume of the at least one component of the formation, wherein the fractional volume is determined based at least in part on the system of equations comprising the first plurality of fractional contributions and the third plurality of fractional contributions, wherein the first plurality of fractional contributions comprises the first plurality of fractional volumes, wherein the sum of the first plurality of fractional volumes is one, wherein the third plurality of fractional contributions comprises a third plurality of fractional volumes, wherein the sum of the third plurality of fractional volumes is one.

2. The system of claim 1 wherein the at least one petrophysical parameter comprises bulk density.

3. The system of claim 1 wherein the at least one petrophysical parameter comprises thermal neutron capture cross-section (Sigma).

4. The system of claim 1 wherein imparting neutrons comprises operating a pulsed neutron source.

5. The system of claim 4 wherein an energy of the neutrons emitted by the pulsed neutron source is approximately 14 MeV.

6. The system of claim 1 wherein the detected radiation events comprise gamma rays resulting from interaction of the neutrons with the formation.

7. The system of claim 6 wherein the gamma rays comprise inelastic scattered gamma rays.

8. The system of claim 6 wherein the gamma rays comprise capture gamma rays.

9. The system of claim 1 wherein the thermal neutron cross-section is determined using an empirical relationship between numbers of detected thermal neutron radiation events and at least one other petrophysical parameter.

10. The system of claim 9 wherein the thermal neutron radiation events are detected at two different distances from a position of imparting the neutrons and the empirical relationship with the at least one other petrophysical parameter is a ratio of numbers of thermal neutron radiation events at each of the two different distances.

11. The system of claim 10 wherein the thermal neutron radiation events comprise capture gamma rays.

12. The system of claim 1 wherein the fast neutron cross-section is determined as a weighted linear combination of a 14-MeV neutron elastic cross section, a 14-MeV neutron inelastic cross section, and an atom density of a formation material.

13. The system of claim 1 wherein the at least one component of the formation comprises at least one of a rock matrix, a porosity, a gas filled porosity, and a liquid filled porosity.

14. The system of claim 1 further comprising a drill string, wherein the well logging instrument is disposed in a part of the drill string.

15. The system of claim 1 wherein the system of equations comprises a system of linear equations.

16. The system of claim 1 wherein the fractional volume is one of the first plurality of fractional volumes.

17. The system of claim 16 wherein the first plurality of fractional volumes and the second plurality of fractional volumes comprise equivalent fractional volumes.

18. The system of claim 1 wherein the at least one component of the formation comprises at least one of a rock matrix, a liquid, and a gas.

19. The system of claim 18 wherein the rock matrix comprises at least two of a sandstone component, a limestone component, a shale component, and a dolomite component.

20. The system of claim 1 wherein the detected radiation events corresponding to the fast neutrons comprise neutron elastic scattering events.

* * * * *